(12) United States Patent
Bremer et al.

(10) Patent No.: US 6,468,608 B1
(45) Date of Patent: Oct. 22, 2002

(54) VINYLENE AND ETHYL COMPOUNDS

(75) Inventors: Matthias Bremer, Darmstadt (DE);
Detlef Pauluth, Ober-Ramstadt (DE);
Kazuaki Tarumi, Seeheim (DE);
Joachim Krause, Dieburg (DE);
Michael Heckmeier, Bensheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/646,923

(22) PCT Filed: Mar. 29, 1999

(86) PCT No.: PCT/EP99/02136

§ 371 (c)(1),
(2), (4) Date: Sep. 25, 2000

(87) PCT Pub. No.: WO99/50210

PCT Pub. Date: Oct. 7, 1999

(30) Foreign Application Priority Data

Apr. 1, 1998 (DE) .......................................... 198 14 550

(51) Int. Cl.⁷ ........................ C09K 19/30; C09K 19/12; C07C 25/24; C07C 43/225
(52) U.S. Cl. .............. 428/1.1; 252/299.63; 252/299.66; 570/129
(58) Field of Search ........................ 252/299.63, 299.66; 428/1.1; 570/127, 129

(56) References Cited

U.S. PATENT DOCUMENTS 6,287,648 B1 * 9/2001 Tarumi et al. ................ 428/1.1

FOREIGN PATENT DOCUMENTS

DE  42 05 970  8/1993
DE  197 07 154  9/1997
EP  0 560 382  9/1993
JP  5-51332  * 3/1993

OTHER PUBLICATIONS

Chemical Abstracts, vol. 120, No. 16, Apr. 18, 1994 abstract No. 204853 & JP 05 279278.
Chemical Abstracts, vol. 119, No. 14, Oct. 4, 1993 abstract No. 149601 & JP 05 085972.
Chemical Abstracts, vol. 118, No. 26, Jun. 28, 1993 abstract No. 264004 & JP 05 070382.

* cited by examiner

*Primary Examiner*—Shean C. Wu
(74) *Attorney, Agent, or Firm*—Millen, White, Zelano & Branigan, P.C.

(57) ABSTRACT

Vinyldene and ethyl compounds of the formula I

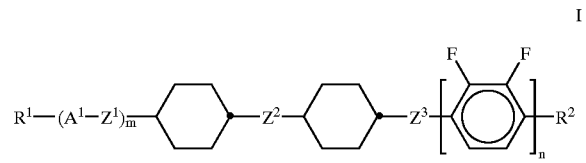

in which $R^1$, $R^2$, $A^1$, $Z^1$, $Z^2$, $Z^3$, m, n and R are as defined herein, where at least one of $Z^1$ to $Z^3$ is

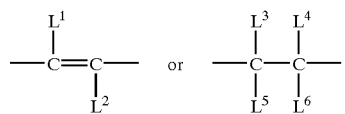

wherein $L^1$ to $L^6$ are each H or F and at least one of $L^1$ to $L^2$ is F or at least one of $L^3$ to $L^6$ is F, are suitable as components of liquid-crystalline media.

30 Claims, No Drawings

VINYLENE AND ETHYL COMPOUNDS

The invention relates to novel vinylidene compounds and ethyl compounds of the formula I

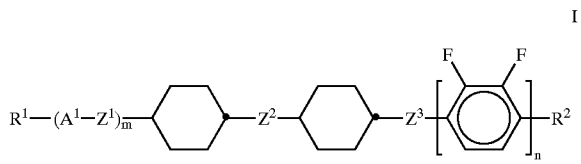

in which
R$^1$ and R$^2$ are each, independently of one another, an alkyl or alkenyl radical having 1 to 15 carbon atoms which is unsubstituted monosubstituted by CN or CF$_{.3}$ or at least monosubstituted by halogen, where one or more CH$_2$ groups in these radicals may also, in each case independently of one another, be replaced by —O—, —S—, —◊——CO—, —CO—O—, —O—CO— or —O—CO—O— in such a way that O atoms are not linked directly to one another,
A$^1$ (a) is a tarns-1,4-cyclohexyl radical, in which, in addition, one or more non-adjacent CH$_2$ groups may be replaced by —O— and/or —S—,
  (b) a 1,4-phenylene radical, in which, in addition, one or two CH groups may be replaced by N,
  (c) a 1,4-cyclohexenylene radical,
  (d) a radical from the group consisting of 1,4-bicyclo [2.2.2]octylene, piperidine-1,4-diyl, naphthalene-2,6-diyl, decahydronaphthalene-2,6-diyl and 1,2,3,4-tetrahydronaphthalene-2,6-diyl,
  where the radicals (a), (b) and (c) may be monosubstituted or polysubstituted by CN or fluorine,
Z$^1$, Z$^2$ or Z$^3$ is each, independently of one another, —CO—O—, —O—CO—, —CH$_2$O—, —OCH$_2$—, —CH$_2$CH$_2$—, —CH=CH—, —C≡C—, —CF$_2$O—, —OCF$_2$—, —(CH$_2$)$_4$— or a single bond,

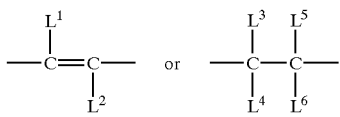

L$^1$ to L$^6$ are each, independently of one another, H or F, where at least one of the radicals L$^1$ and L$^2$ is F or L$^3$ to L$^6$ are F and the other radical L$^1$ or L$^2$ is H or F and the other radicals L$^3$ to L$^6$ are H or F,
m is 0 or 1, and
n is 1 or 2,
with the proviso that at least one bridge Z$^1$, Z$^2$ or Z$^3$ is

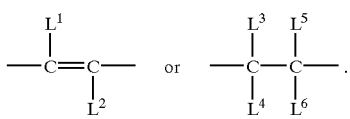

The invention furthermore relates to the use of these compounds as components of liquid-crystalline media, and to liquid-crystal and electro-optical display elements which contain the novel liquid crystalline media.

The compounds of the formula I can be used as components of liquid-crystalline media, in particular for displays based on the principle of the twisted cell, the guest-host effect, the effect of deformation of aligned phases or the effect of dynamic scattering.

The compounds of the formula I are distinguished by clearly negative anisotropy of the dielectric constant and are aligned in an electric field with their longitudinal molecular axes perpendicular to the field direction. This effect is known and is utilized to control the optical transparency in various liquid-crystal displays, for example in liquid-crystal cells of the light-scattering type (dynamic scattering), of the DAP (deformation of aligned phases) type, of the ECB (electrically controlled birefringence) type or of the guest-host interaction type.

Compounds of the formula I are furthermore suitable as components of chiral tilted smectic phases. Chiral tilted smectic liquid-crystalline phases having ferroelectric properties can be prepared by adding a suitable chiral dopant to base mixtures having one or more tilted smectic phases (L. A. Veresnev et al., Mol. Cryst. Liq. Cryst. 89, 327 (1982); H. R. Brand et al., J. Physique 44 (lett.), L-771 (1983). Such phases can be used as dielectrics for fast-switching displays based on the principle of SSFLC technology described by Clark and Lagerwall (N. A. Clark and S. T. Lagerwall, Appl. Phys. Lett. 36, 899 (1980); U.S. Pat. No. 4,367,924) on the basis of the ferroelectric properties of the chiral tilted phase.

A number of liquid-crystalline compounds having slightly negative dielectric anisotropy have already been synthesized. By contrast, relatively few liquid-crystal components having highly negative anisotropy of the dielectric constant are known. Moreover, the latter generally have disadvantages, such as, for example, poor solubility in mixtures, high viscosity, high melting points and chemical instability. There is thus a demand for further compounds having negative dielectric anisotropy which allow the properties of mixtures to be further improved for a wide variety of electro-optical applications.

Liquid-crystal compounds having negative dielectric anisotropy which contain two or three rings linked via carboxyl groups or covalent bonds and one or more side groups, such as halogen, cyano or nitro groups, are disclosed in DE 22 40 864, DE 26 13 293, DE 28 35 662, DE 28 36 086, EP 023 728, EP 0 084 194 and EP 0 364 538.

JP 05 070 382 covers, in a broad generic formula, the transmonofluoroethylene compounds claimed here. The prior art thus neither reveals to the person skilled in the art possible syntheses of the claimed compounds having negative dielectric anisotropy in a simple manner nor suggests that the compounds according to the invention have favourably located mesophase ranges and are distinguished by large negative dielectric anisotropy at the same time as low viscosity and have increased low-temperature stability.

The invention had the object of indicating stable, liquid-crystalline or mesogenic compounds having a large negative dielectric anisotropy and at the same time low viscosity and high low-temperature stability, with an unrestricted nematic phase range.

It has been found that the compounds of the formula I are eminently suitable as components of liquid-crystalline phases. In particular, they can be used to prepare stable liquid-crystalline phases having a broad mesophase range and comparatively low viscosity and high low-temperature stability.

The compounds of the formula I are furthermore suitable as components of chiral tilted smectic liquid-crystalline phases.

In addition, the provision of the compounds of the formula I generally considerably broadens the range of liquid-crystalline substances which are suitable, from various applicational points of view, for the preparation of liquid-crystalline mixtures.

The compounds of the formula I have a broad range of applications. Depending on the choice of substituents, these compounds can be used as base materials of which liquid-crystalline phases are predominantly composed; however, compounds of the formula I can also be added to liquid-crystalline base materials from other classes of compound in order, for example, to vary the dielectric and/or optical anisotropy and/or the viscosity and/or the spontaneous polarization and/or the phase ranges and/or the tilt angle and/or the pitch of a dielectric of this type.

The compounds of the formula I are furthermore suitable as intermediates in the preparation of other substances which can be used as constituents of liquid-crystalline dielectrics.

In the pure state, the compounds of the formula I are colourless and form liquid-crystalline mesophases in a temperature range which is favourably located for electro-optical use. They are very stable chemically, thermally and to light.

The invention thus relates to the compounds of the formula I. The invention furthermore relates to the use of the compounds of the formula I as components of liquid-crystalline mixtures. The invention furthermore relates to liquid-crystalline phases containing at least one compound of the formula I, and to liquid-crystal display elements containing such phases. The compounds are distinguished, in liquid-crystal mixtures, by the fact that low viscosity and an increase in the low-temperature stability are achieved, with an unrestricted nematic phase range.

In the compounds of the formulae above and below, each $R^1$, independently of the others, is preferably straight-chain alkyl, 1E-alkenyl or 3E-alkenyl, and $R^2$ is preferably straight-chain alkoxy having 1–5 carbon atoms, in particular $OCH_3$ or $OC_2H_5$, furthermore alkyl having 1–5 carbon atoms, in particular $CH_3$ or $C_2H_5$.

Preference is furthermore given to compounds of the formulae above and below in which $R^1$ is alkoxy or oxaalkyl (for example alkoxymethyl).

$Z^1$, $Z^2$ and $Z^3$ are each, independently of one another, preferably a single bond or a —$C_2H_4$— bridge.

The radicals $R^1$ and $R^2$ in the formulae above and below preferably have 2–12 carbon atoms, in particular 3–10 carbon atoms. One or two $CH_2$ groups in $R^1$ and $R^2$ may also be replaced. Preferably, only one $CH_2$ group is replaced, by —O— or —CH=CH—.

In the formulae above and below, the radicals $R^1$ and $R^2$ are preferably alkyl, alkoxy or another oxaalkyl group, furthermore alkyl groups in which one or two $CH_2$ groups may be replaced by —CH=CH—.

If the radicals $R^1$ and $R^2$ are alkyl radicals in which one ("alkoxy" or "oxaalkyl") or two ("alkoxyalkoxy" or "dioxaalkyl") non-adjacent $CH_2$ group(s) may be replaced by O atoms, they may be straight-chain or branched. They are preferably straight-chain, have 2, 3, 4, 5, 6 or 7 carbon atoms and accordingly are preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoxy, undecoxy or dodecoxy.

Oxaalkyl is preferably straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl, 1,3-dioxabutyl (=methoxymethoxy), 1,3-, 1,4- or 2,4-dioxapentyl, 1,3-, 1,4-, 1,5-, 2,4-, 2,5- or 3,5-dioxahexyl, 1,3-, 1,4-, 1,5-, 1,6-, 2,4-, 2,5-, 2,6-, 3,5-, 3,6- or 4,6-dioxaheptyl.

If the radicals $R^1$ and $R^2$ are an alkyl radical in which one $CH_2$ group has been replaced by —CH=CH—, the trans-form is preferred. This alkenyl radical may be straight-chain or branched. It is preferably straight-chain and has 2 to 10 carbon atoms. Accordingly, it is in particular vinyl, prop-1- or prop-2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -8- or -9-enyl.

Compounds of the formula I containing branched radicals $R^1$ may occasionally be of importance owing to better solubility in conventional liquid-crystalline base materials, but in particular as chiral dopants if they are optically active. Smectic compounds of this type are suitable as components of ferroelectric materials.

Branched groups of this type generally contain not more than one chain branch. Preferred branched radicals $R^1$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl, 3-oxa-4-methylpentyl, 4-methylhexyl, 2-nonyl, 2-decyl, 2-dodecyl or 6-methyloctoxy.

Formula I covers the racemates of these compounds and the optical antipodes, and mixtures thereof.

Of the compounds of the formula I, preference is given to those in which at least one of the radicals present therein has one of the preferred meanings given.

In the compounds of the formula I, preference is given to those stereoisomers in which the rings Cyc and piperidinyl are trans-1,4-disubstituted. Those of the abovementioned formulae which contain one or more Pyd, Pyr and/or Dio groups in each case include the two 2,5-positional isomers.

A very particularly preferred smaller group of compounds consists of those of the subformulae I1 to I5:

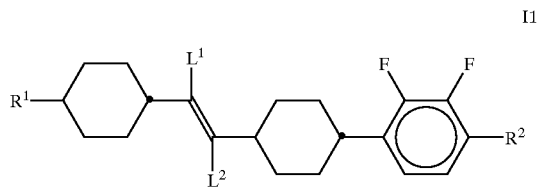

I1

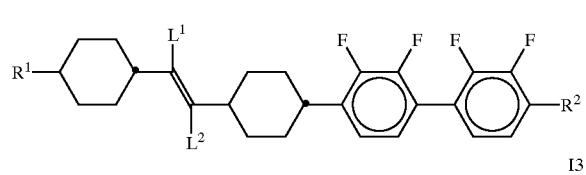

I2

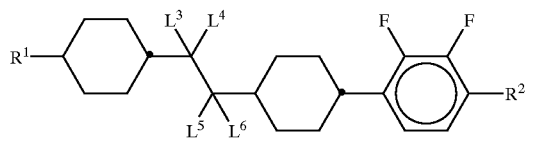

I3

I4

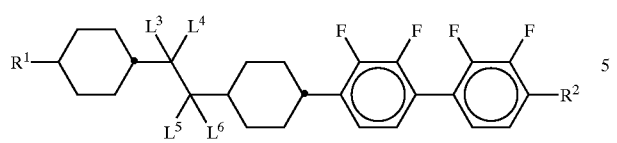

I5

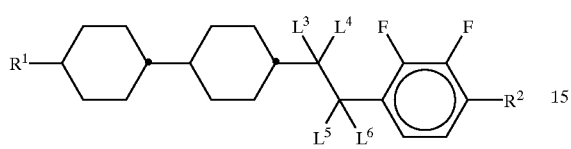

Particular preference is given to compounds of the formulae I1 and I3.

In the compounds of the formula I and in the subformulae I1 and I2, $R^2$ is preferably methoxy, ethoxy, propoxy, butoxy, pentoxy, hexoxy, furthermore methyl, ethyl, n-propyl, n-butyl, n-pentyl or n-hexyl.

$R^1$ is preferably ethyl, propyl, n-butyl, n-pentyl, n-hexyl, vinyl, 1E-propenyl, 1E-butenyl, 1E-pentenyl, 1E-hexenyl, 1E-heptenyl, 1E-octenyl, 1E-nonenyl, 1E-decenyl, allyl, 2Z-butenyl, 2Z-pentenyl, 2Z-hexenyl, 2Z-heptenyl, 2Z-octenyl, 2Z-nonenyl, 2Z-decenyl, 3E-butenyl, 3E-pentenyl, 3E-hexenyl, 3E-heptenyl, 3E-octenyl, 3E-nonenyl or 4E-pentenyl.

$L^1$ and $L^2$ are preferably fluorine. Particular preference is given to compounds of the formula I in which $L^1$=F and $L^2$=H or F, or $L^1$=H or F and $L^2$=F, and to compounds of the formula I3 in which $L^3$=$L^4$=H and $L^5$=$L^6$=F or $L^3$–$L^6$=F.

The compounds of the formula I are prepared by methods known per se, as described in the literature (for example in the standard works, such as Houben-Weyl, Methoden der Organischen Chemie [Methods of Organic Chemistry], Georg-Thieme-Verlag, Stuttgart), to be precise under reaction conditions which are known and suitable for said reactions.

Use can also be made here of variants which are known per se, but are not mentioned here in greater detail.

Compounds according to the invention can be prepared, for example, by reacting benzene derivatives as shown in the following reaction schemes:

Scheme 1

1. BuLi
2. 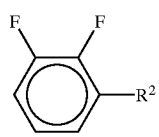
3. $H^+$/-$H_2O$
4. $H_2$, cat.

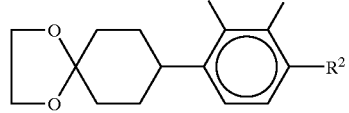

↓ $H_3O^+$

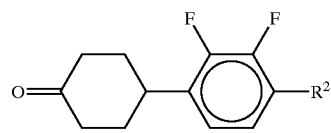

1. $CH_3OCH$=$PPh_3$
2. $H^+$
3. NaOH/MeOH (cis/trans isomerization)

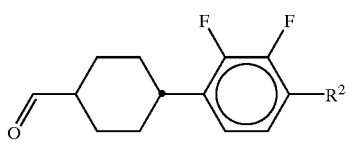

Li powder

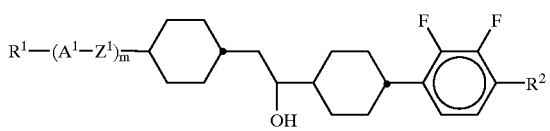

↓

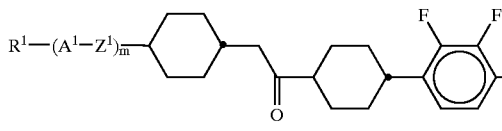

↓ Jones oxidation

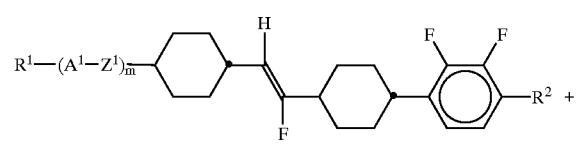

↓ DAST or MOST

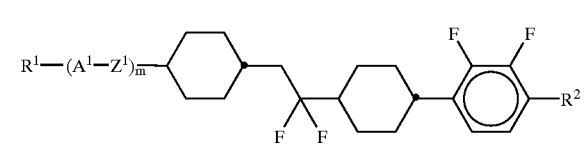

+

Particularly preferred compounds are prepared as follows:
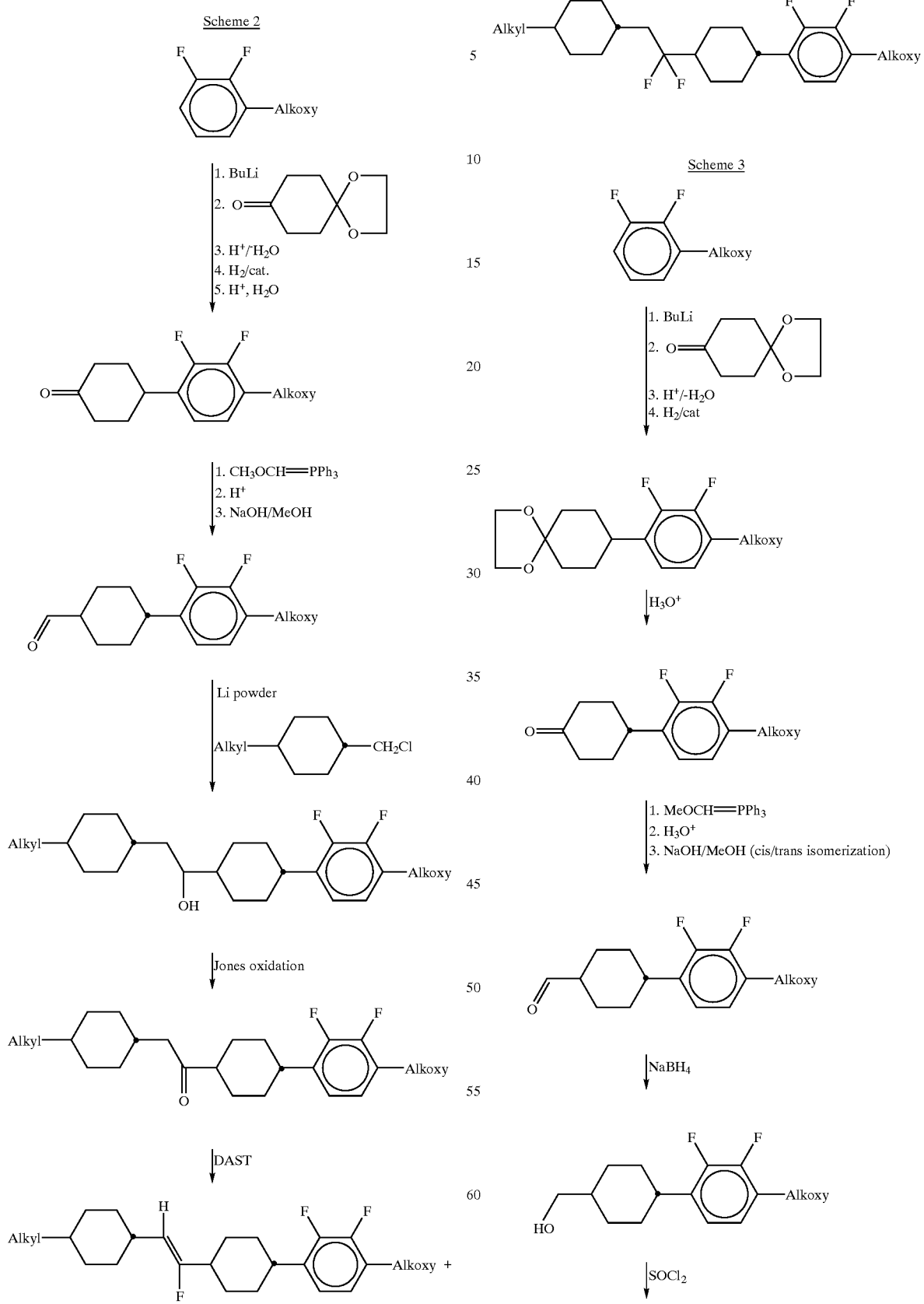

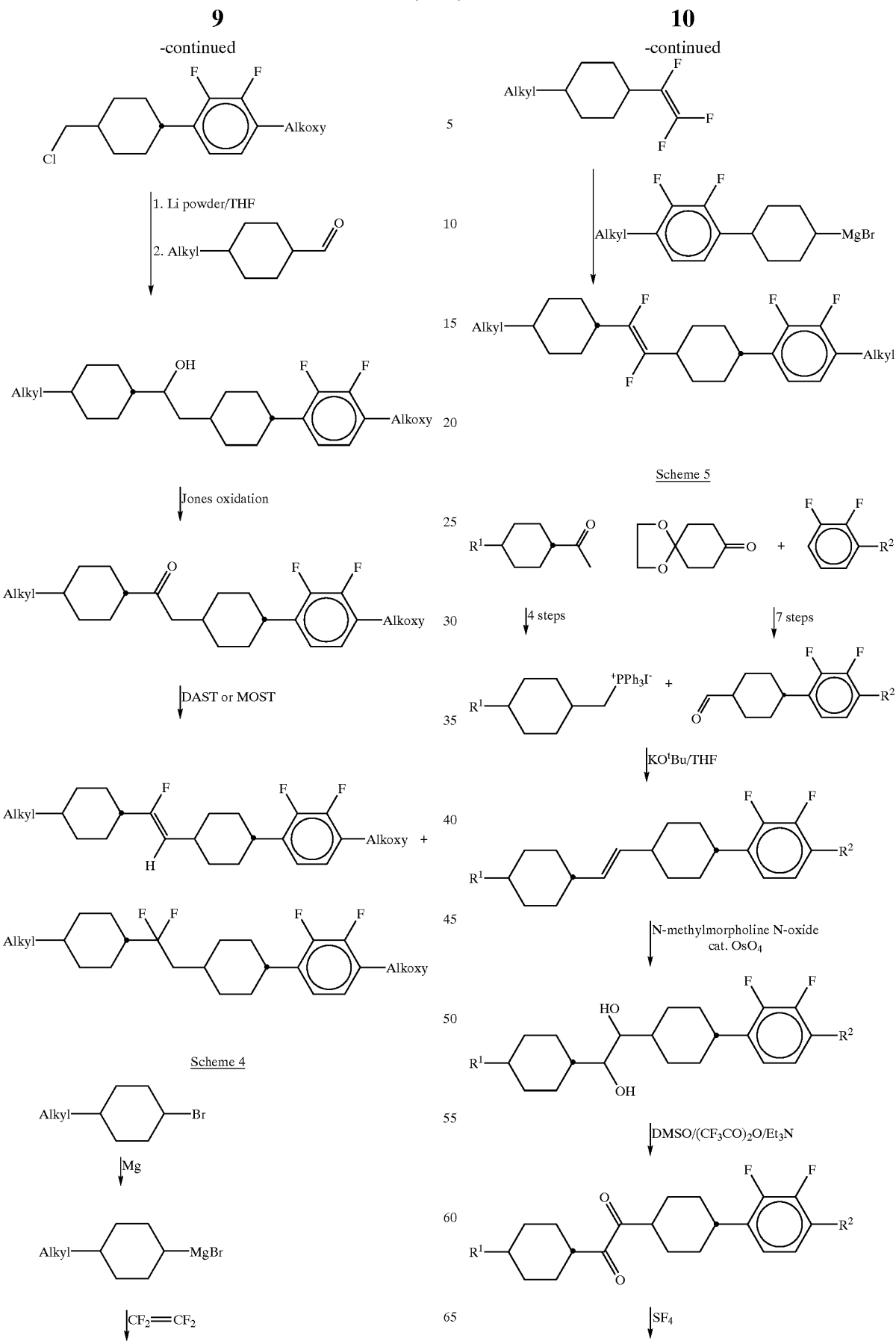

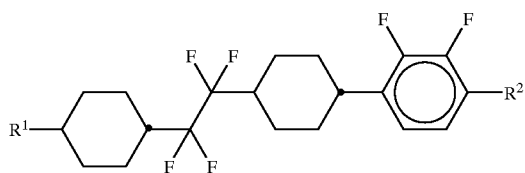

Scheme 6

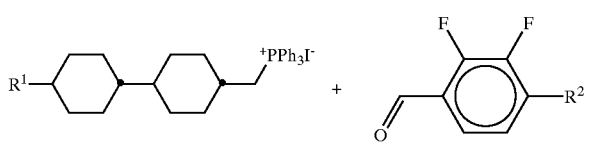

↓ KO$^t$Bu/THF

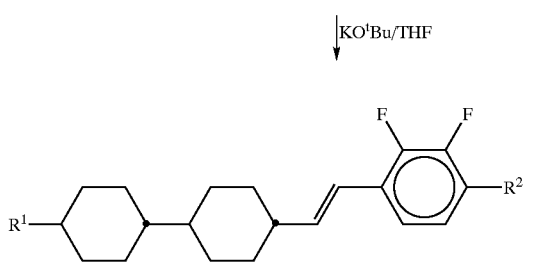

↓ N-methylmorphine N-oxide
  cat. OsO$_4$

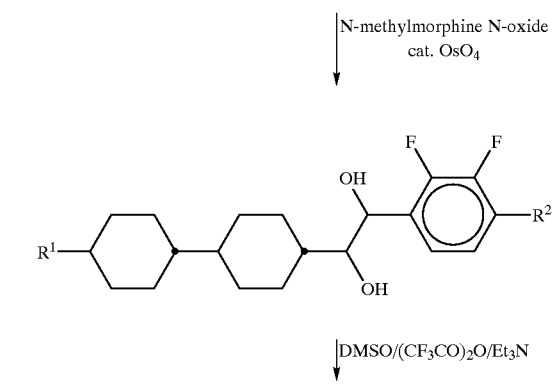

↓ DMSO/(CF$_3$CO)$_2$O/Et$_3$N

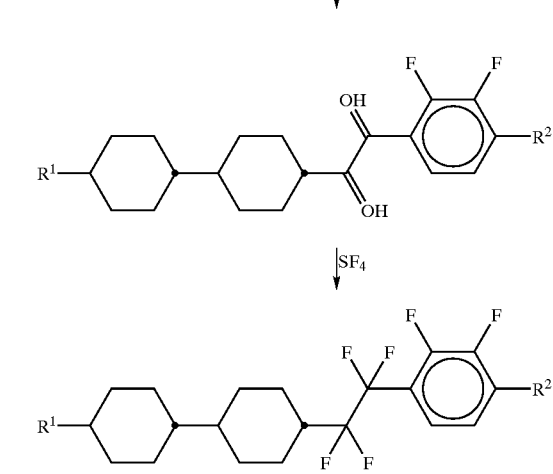

The invention likewise relates to a process for the preparation of —C$_2$F$_4$-bridged alkyl compounds starting from compounds which contain a

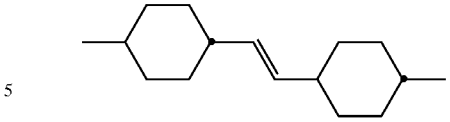

structural unit, conversion of the double bond into the dihydroxyl compound which contains a

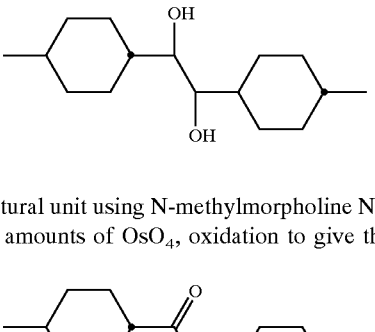

structural unit using N-methylmorpholine N-oxide and catalytic amounts of OsO$_4$, oxidation to give the diketone

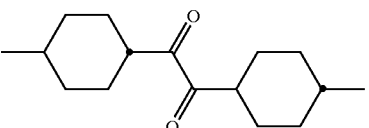

and reaction with SF$_4$ under reduced pressure to give the —C$_2$F$_4$— structural unit

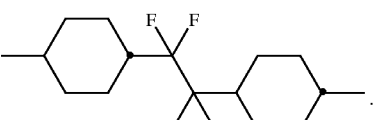

The compounds of the formula I are prepared by methods known per se, as described in the literature (for example in standard works, such as Houben-Weyl, Methoden der Organischen Chemie [Methods of Organic Chemistry], Georg-Thieme-Verlag, Stuttgart), to be precise under reaction conditions which are known and suitable for said reactions. Use can also be made here of variants which are known per se, but are not mentioned here in greater detail.

If desired, the starting materials can also be formed in situ by not isolating them from the reaction fixture, but instead immediately converting them further into the compounds of the formula I.

Compounds of the formula I are obtainable starting from 1,2-difluorobenzene. This is metallated by known processes (for example A. M. Roe et al., J. Chem. Soc. Chem. Comm., 22, 582 (1965)) and reacted with the corresponding electrophile. This reaction sequence can be carried out a second time with the resultant 1-substituted 2,3-difluorobenzene using a suitable electrophile, giving 1,4-disubstituted 2,3-difluorobenzenes, which can be converted, if desired, into the end products in further reaction steps. 1,2-Difluorobenzene or 1-substituted 2,3-difluorobenzene is reacted with phenyllithium, lithium tetramethylpiperidine, n-, sec- or tert-butyllithium at temperatures of from −100° C. to +50° C., preferably from −78° C. to 0° C., in an inert solvent, such as diethyl ether, tetrahydrofuran, dimethoxyethane, tert-butyl methyl ether or dioxane, hydrocarbons, such as hexane, heptane, cyclohexane, benzene or toluene, or mixtures of these solvents, if desired with addition of a complexing agent, such as tetramethylethylenediamine (TMEDA) or hexamethylphosphoric triamide.

The lithium 2,3-difluorophenyl compounds are reacted with the corresponding electrophiles at from −100° C. to 0° C., preferably at below −50° C. Suitable electrophiles are aldehydes, ketones, nitriles, epoxides, carboxylic acid derivatives, such as esters, anhydrides or halides, haloformic esters or carbon dioxide.

For the reaction with aliphatic or aromatic halogen compounds, the lithium 2,3-difluorophenyl compounds are transmetallated and coupled with transition-metal catalysis. The zinc (cf. DE-A 36 32 410) or titanium 2,3-difluorophenyl compounds (cf. DE-A 37 36 489) are particularly suitable for this purpose.

Suitable reducible groups are preferably carbonyl groups, in particular keto groups, furthermore, for example, free or esterified hydroxyl groups or aromatically bonded halogen atoms. Preferred starting materials for the reduction conform to the formula I, but may contain a cyclohexene ring or cyclohexanone ring in place of a cyclohexane ring and/or a —CH=CH— group in place of a —CH$_2$CH$_2$— group and/or a —CO— group in place of a —CH$_2$— group and/or a free or functionally modified (for example in the form of its p-toluenesulfonate) OH group in place of an H atom.

The reduction can be carried out, for example, by catalytic hydrogenation at temperatures between 0° C. and about 200° C. and at pressures between about 1 and 200 bar in an inert solvent, for example an alcohol, such as methanol, ethanol or isopropanol, an ether, such as tetrahydrofuran (THF) or dioxane, an ester, such as ethyl acetate, a carboxylic acid, such as acetic acid, or a hydrocarbon, such as cyclohexane. Suitable catalysts are advantageously noble metals, such as Pt or Pd, which can be employed in the form of oxides (for example PtO$_2$ or PdO), on a support (for example Pd on charcoal, calcium carbonate or strontium carbonate) or in finely divided form.

Ketones can also be reduced by the methods of Clemmensen (using zinc, zinc amalgam or tin and hydrochloric acid, advantageously in aqueous-alcoholic solution or in the heterogeneous phase with water/toluene at temperatures between about 80° C. and 120° C.) or Cagliotti [by reacting the tosyl hydrazones with sodium borohydride, sodium cyanoborohydride or catecholborane (Org. Synth. 52, 122 (1972))] to give the corresponding compounds of the formula I containing alkyl groups and/or —CH$_2$CH$_2$— bridges.

Reductions using complex hydrides are also possible. For example, arylsulfonyloxy groups can be removed reductively using LiAlH$_4$, in particular p-toluenesulfonyloxymethyl groups can be reduced to methyl groups, advantageously in an inert solvent, such as diethyl ether or THF, at temperatures between about 0 and 100° C.

The esters according to the invention can be prepared by esterifying corresponding carboxylic acids (or reactive derivatives thereof) using alcohols or phenols (or reactive derivatives thereof).

Suitable reactive derivatives of said carboxylic acids are, in particular, the acid halides, especially the chlorides and bromides, furthermore the anhydrides, for example including mixed anhydrides, azides or esters, in particular alkyl esters having 1–4 carbon atoms in the alkyl group.

Suitable reactive derivatives of said alcohols or phenols are, in particular, the corresponding metal alkoxides or phenoxides, preferably of an alkali metal, such as Na or K.

The esterification is advantageously carried out in the presence of an inert solvent. Highly suitable solvents are, in particular, ethers, such as diethyl ether, di-n-butyl ether, THF, dioxane or anisole, ketones, such as acetone, butanone or cyclohexanone, amides, such as DMF or hexamethylphosphoric triamide, hydrocarbons, such as benzene, toluene or xylene, halogenated hydrocarbons, such as tetrachloromethane or tetrachloroethylene, and sulfoxides, such as dimethyl sulfoxide or sulfolane. Water-immiscible solvents may advantageously be used at the same time for removal by azeotropic distillation of the water formed in the esterification. An excess of an organic base, for example pyridine, quinoline or triethylamine, as solvent for the esterification may sometimes also be used. The esterification can also be carried out in the absence of a solvent, for example by simply heating the components in the presence of sodium acetate. The reaction temperature is usually between −50° and +250° C., preferably between −20° C. and +80° C. At these temperatures, the esterification reactions are generally complete after 15 minutes to 48 hours.

In detail, the reaction conditions for the esterification depend substantially on the nature of the starting materials used. For example, a free carboxylic acid is generally reacted with a free alcohol or phenol in the presence of a strong acid, for example a mineral acid, such as hydrochloric acid or sulfuric acid. A preferred reaction procedure is to react an acid anhydride or in particular an acid chloride with an alcohol, preferably in a basic medium, suitable bases being, in particular alkali metal hydroxides, such as sodium hydroxide or potassium hydroxide, alkali metal carbonates or hydrogencarbonates, such as sodium carbonate, sodium hydrogencarbonate, potassium carbonate or potassium hydrogencarbonate, alkali metal acetates, such as sodium acetate or potassium acetate, alkaline earth metal hydroxides, such as calcium hydroxide, or organic bases, such as triethylamine, pyridine, lutidine, collidine or quinoline. A further preferred embodiment of the esterification comprises first converting the alcohol or phenol into the sodium or potassium alkoxide or phenoxide, for example by treatment with ethanolic sodium hydroxide solution or potassium hydroxide solution, isolating the alkoxide or phenoxide and suspending it in acetone or diethyl ether with stirring together with sodium hydrogencarbonate or potassium carbonate, and treating the suspension with a solution of the acid chloride or anhydride in diethyl ether, acetone or DMF, advantageously at temperatures between about −25° C. and +20° C.

Ethers according to the invention are obtainable by etherifying corresponding hydroxyl compounds, preferably corresponding phenols, where the hydroxyl compound is advantageously first converted into a corresponding metal derivative, for example into the corresponding alkali metal alkoxide or alkali metal phenoxide by treatment with NaH, NaNH$_2$, NaOH, KOH, Na$_2$CO$_3$ or K$_2$CO$_3$. This alkoxide or phenoxide can then be reacted with the corresponding alkyl halide, alkyl sulfonate or dialkyl sulfate, advantageously in an inert solvent, such as acetone, 1,3-dimethoxyethane, DMF or dimethyl sulfoxide, or alternatively in an excess of aqueous or aqueous-alcoholic NaOH or KOH, at temperatures between about 20° C. and 100° C.

The liquid-crystalline phases according to the invention consist of 2 to 25, preferably 3 to 15 components, including at least one compound of the formula I. Particularly preferred mixtures comprise one, two, three or four compounds of the formula I, preferably one or two compounds of the formula I. The other constituents are preferably selected from nematic or nematogenic substances, in particular known substances, from the classes consisting of the azoxybenzenes, benzylideneanilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylnaphthalenes, 1,4-bis-cyclohexylbenzenes, 4,4'-bis-cyclohexylbiphenyls, phenyl- or cyclohexylpyrimidines, phenyl- or cyclohexyldioxanes, phenyl- or cyclohexyldithianes, 1,2-di-phenylethanes, 1,2-dicyclohexylethanes, 1-phenyl-2-cyclohexylethanes, optionally halogenated stilbenes, benzyl phenyl ethers, tolans and substituted cinnamic acids.

The most important compounds which are suitable as constituents of liquid-crystalline phases of this type can be characterized by the formula 2

in which L and E are each a carbocyclic or heterocyclic ring system from the group consisting of 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, di- and tetrahydronaphthalene, quinazoline and tetrahydroquinazoline, G is —CH=CH— —N(O)=N—
—CH=CY— —CH=N(O)—
—C≡C— —CH$_2$—CH$_2$—
—CO—O— —CH$_2$—O—
—CO—S— —CH$_2$—S—
—CH=N— —COO-Phe-COO— or a C—C single bond, where Y is halogen, preferably chlorine, or —CN, and R' and R" are alkyl, alkoxy, alkanoyloxy or alkoxycarbonyloxy having up to 18, preferably up to 8, carbon atoms, or one of these radicals is alternatively CN, NC, NO$_2$, OCF$_3$, CF$_3$, F, Cl or Br.

In most of these compounds, R' and R" are different from one another, one of these radicals usually being an alkyl or alkoxy group. However, other variants of the proposed substituents are also common. Many such substances or mixtures thereof are commercially available. All these substances can be prepared by methods which are known from the literature.

Besides one, two, three, four or more compounds of the formula I, the preferred mixtures comprise, in particular, one or more compounds of the components listed below:

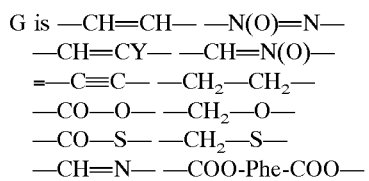

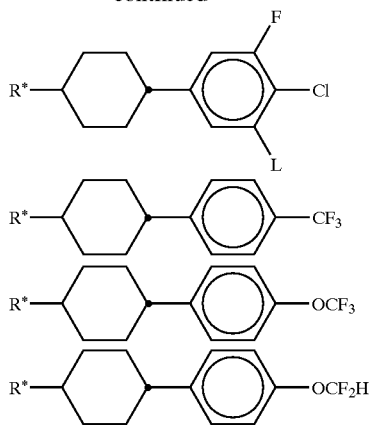

-continued

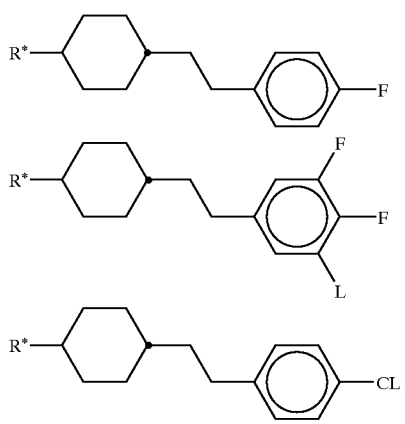

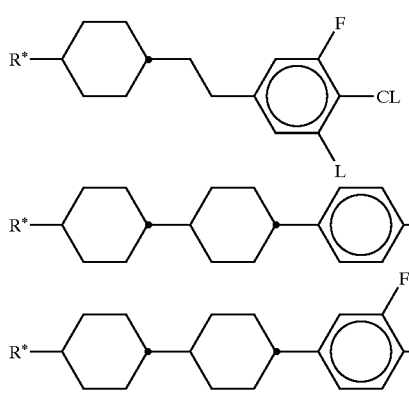

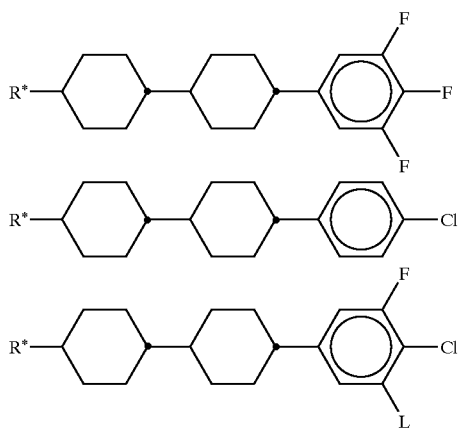

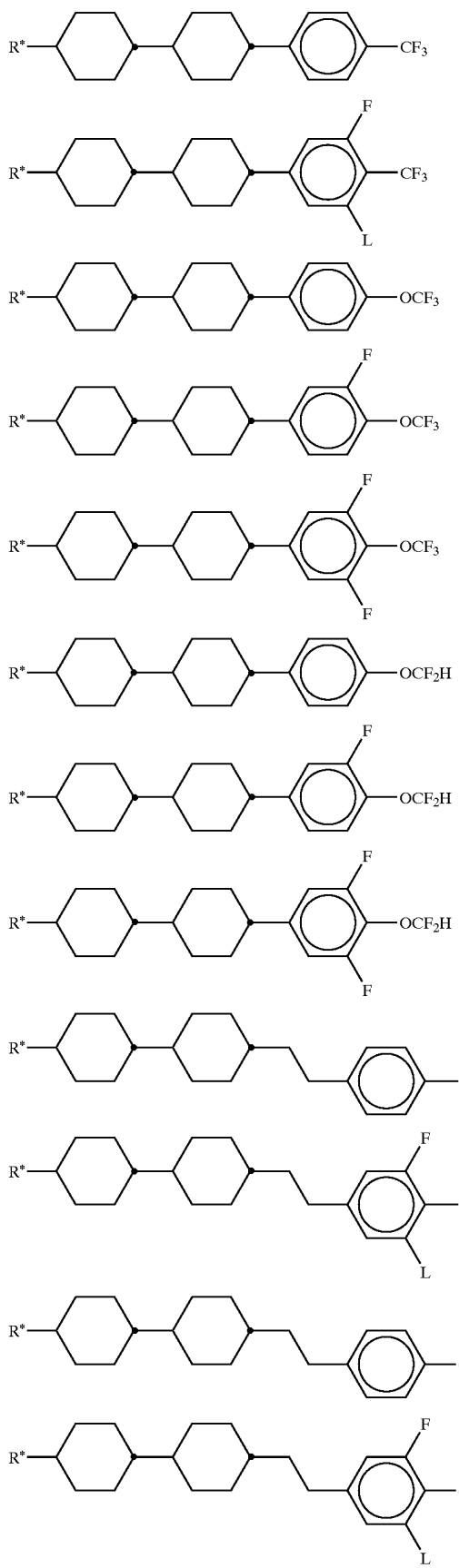
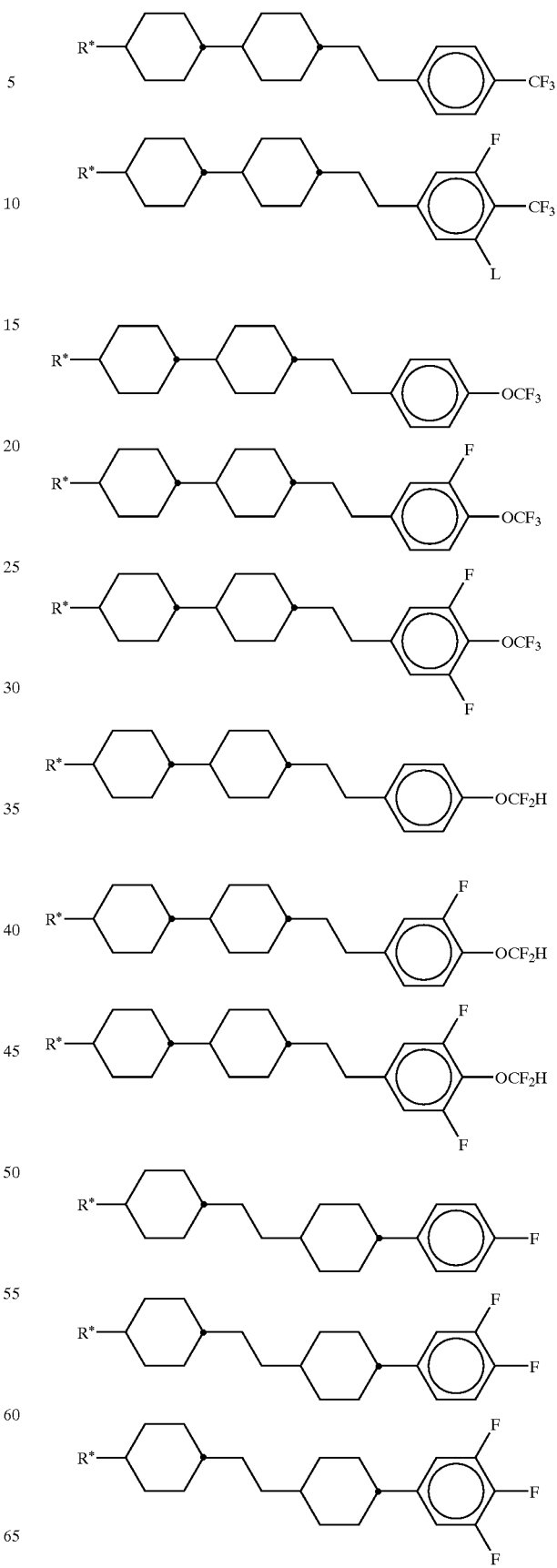

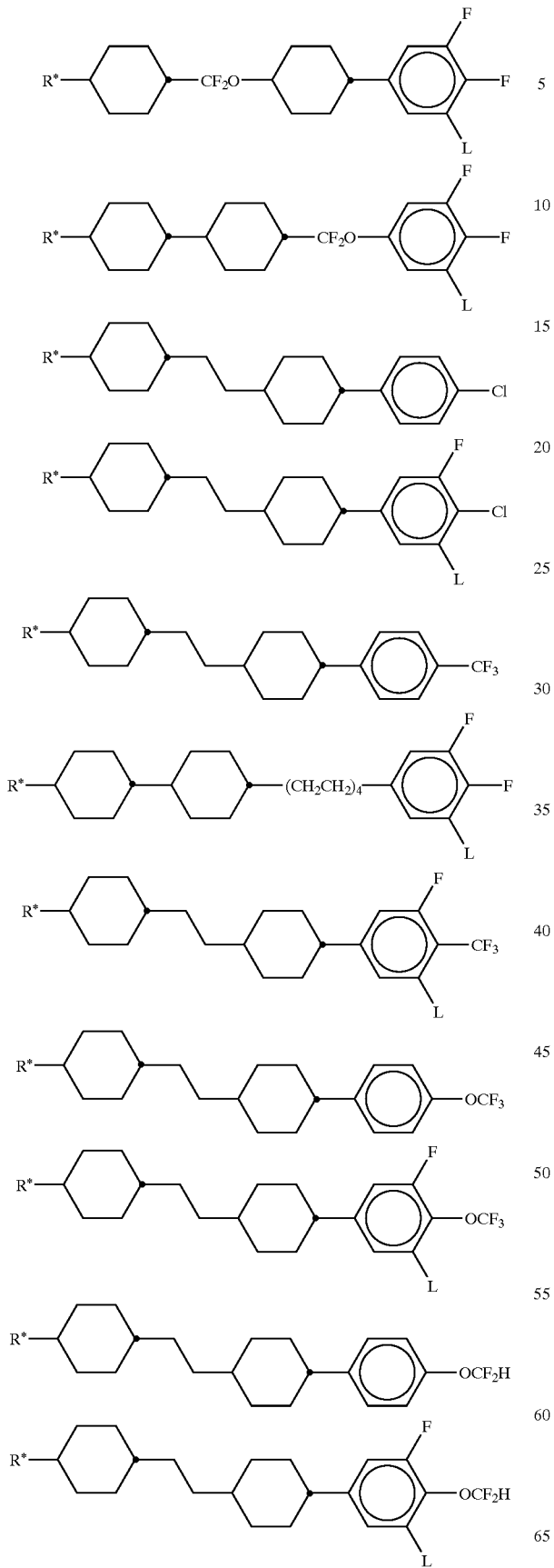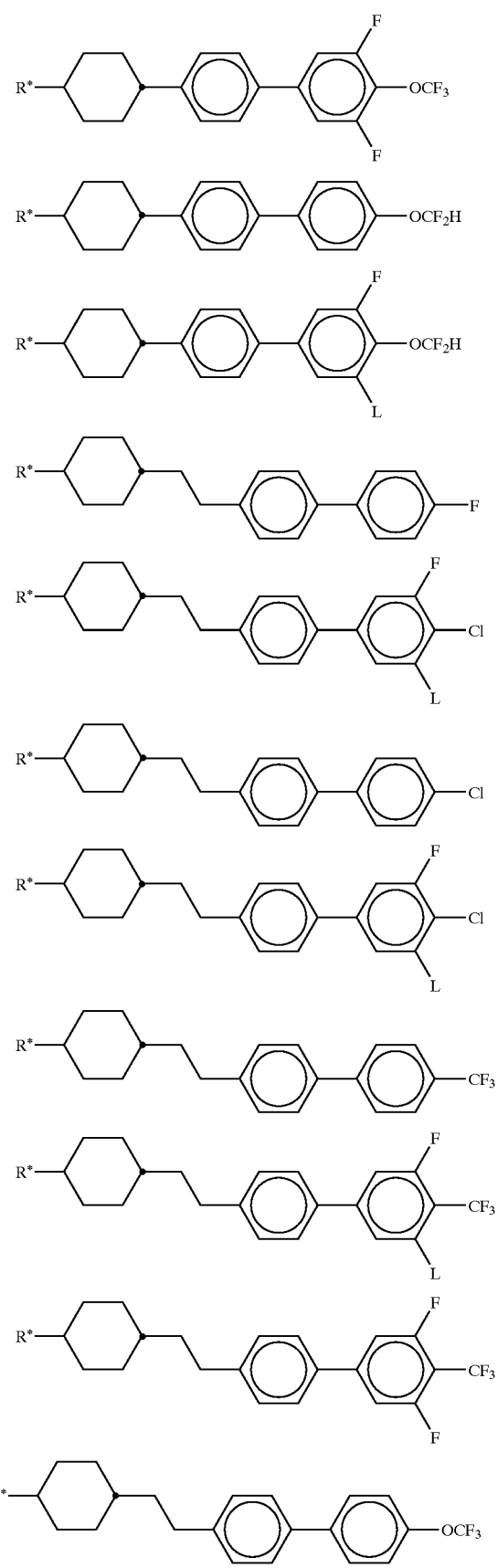

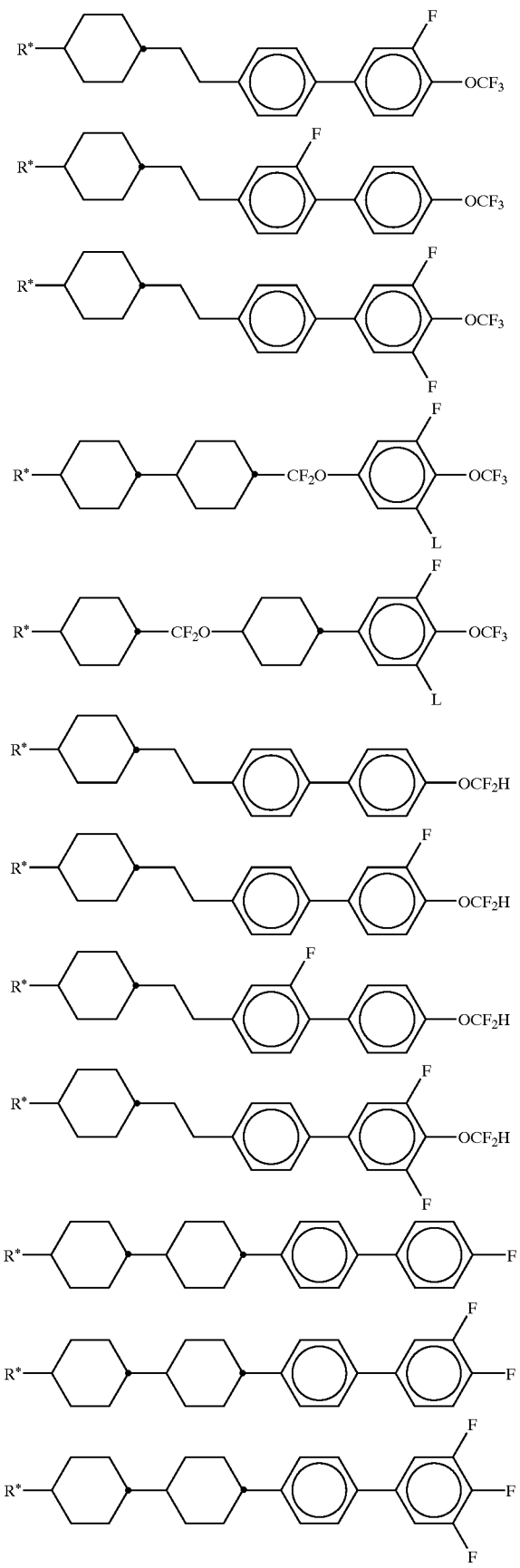
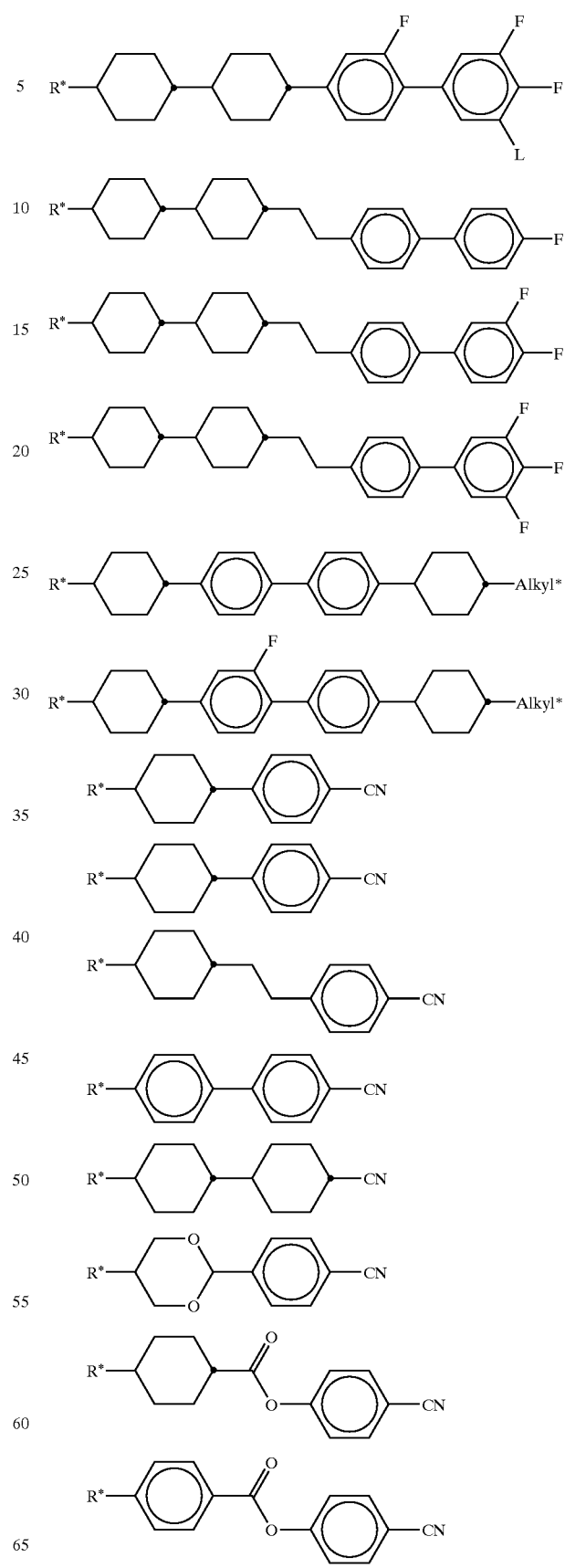

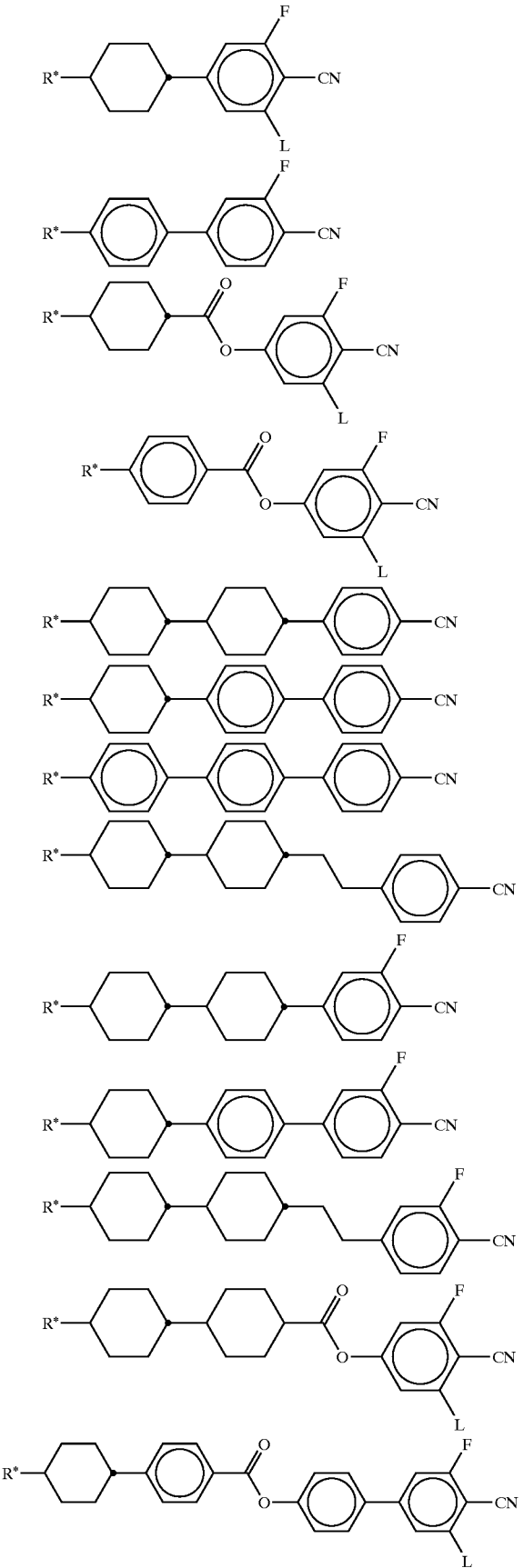
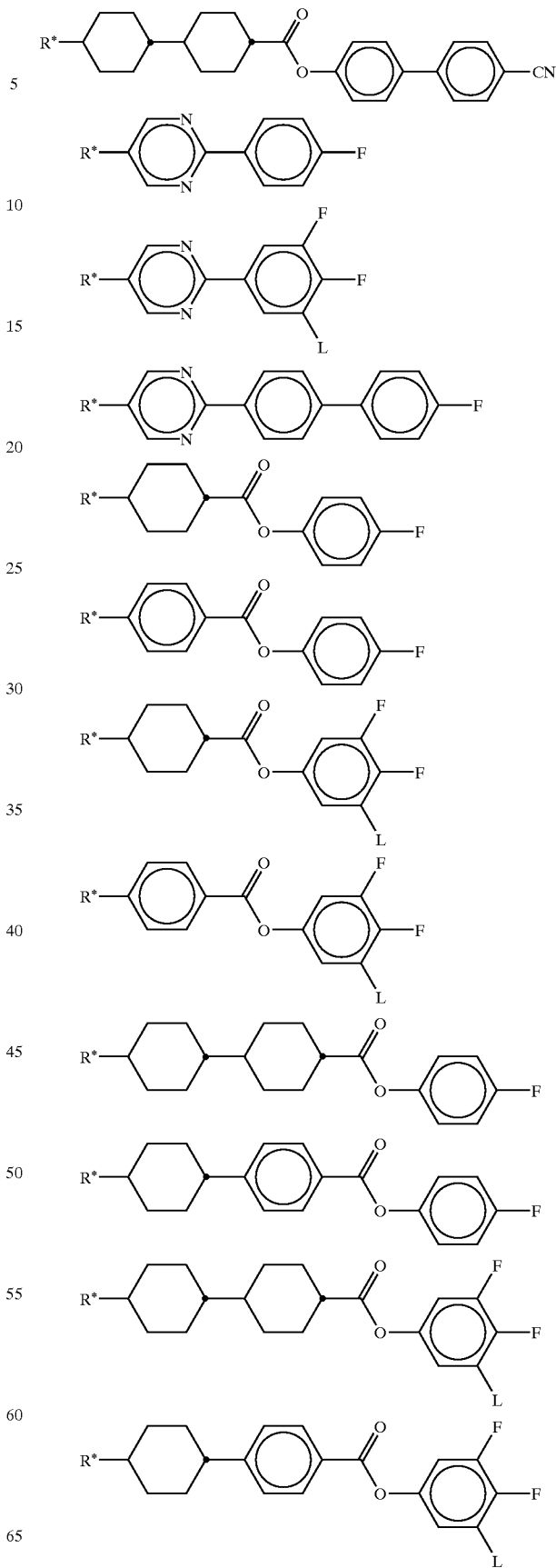

-continued
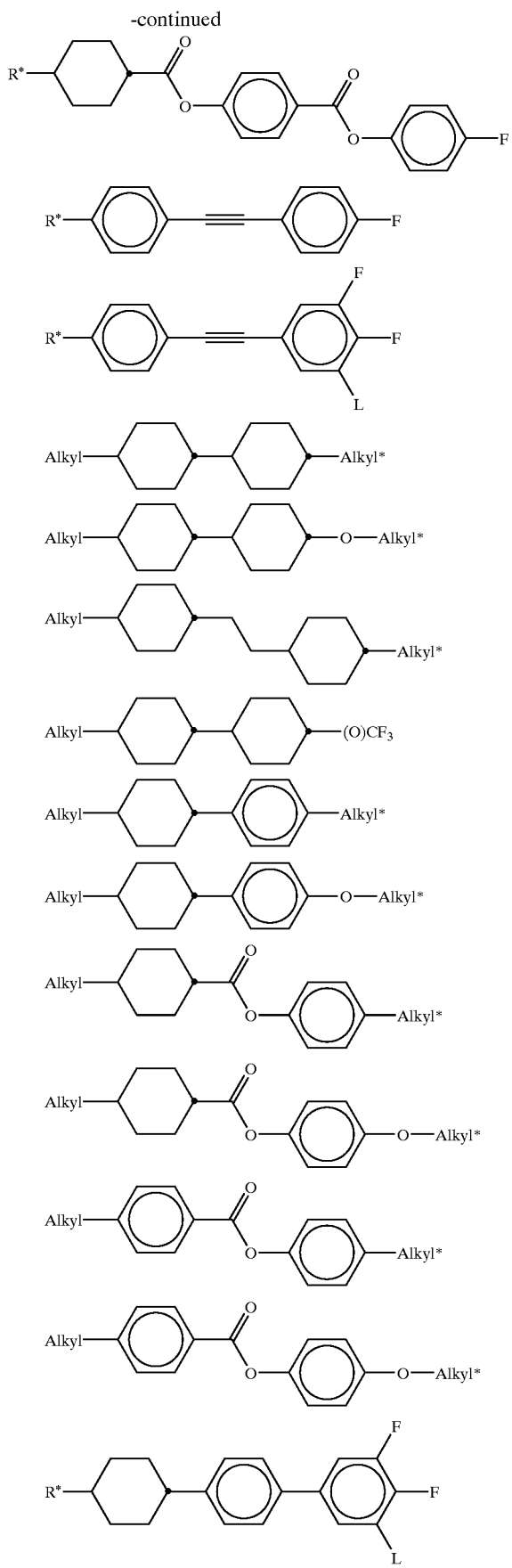
-continued
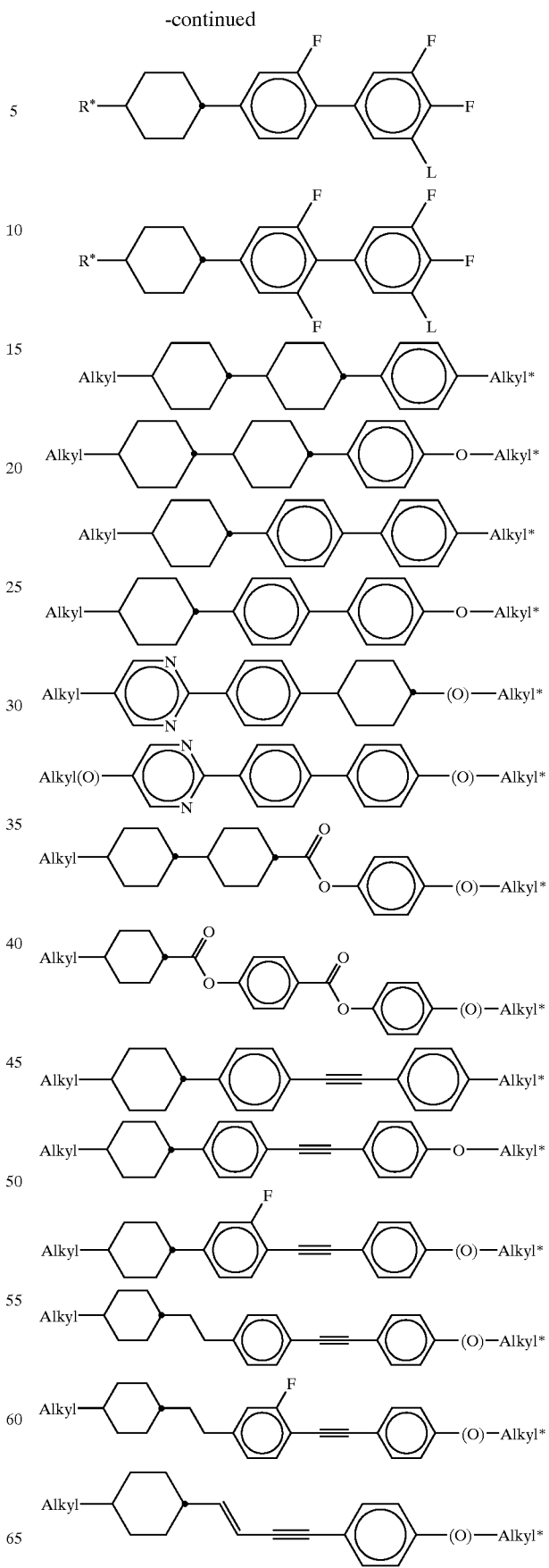

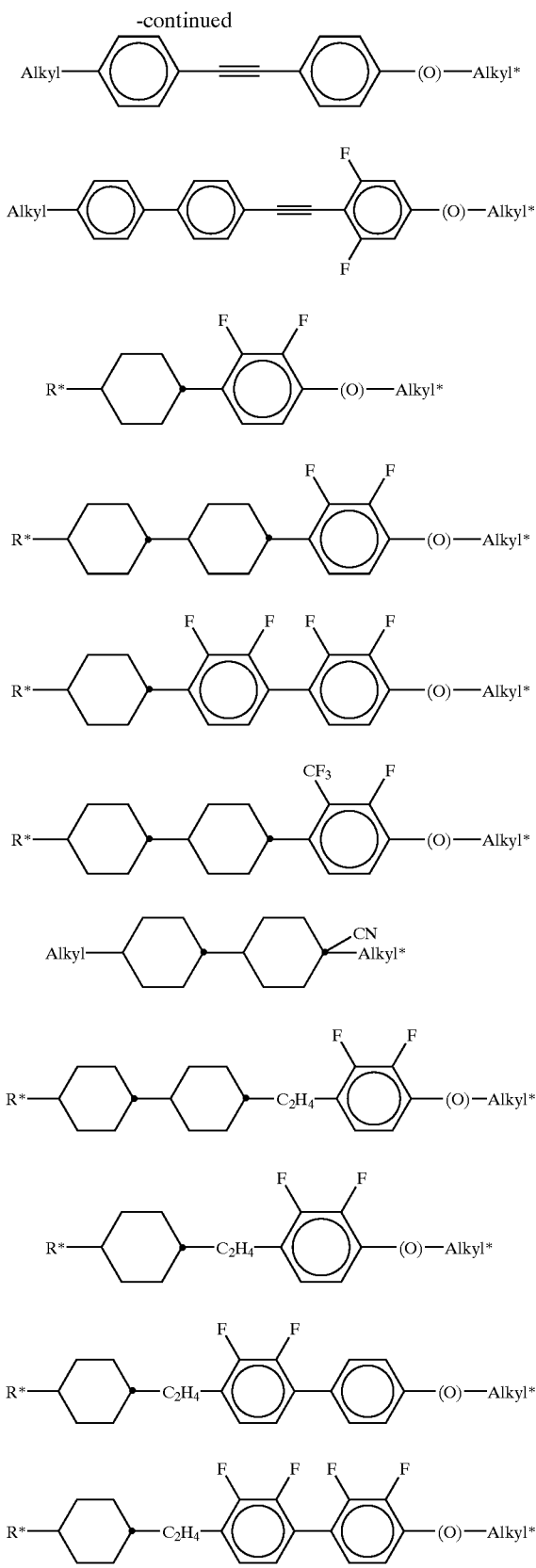

in which
R* is as defined for $R^1$ or $R^2$ and is preferably straight-chain alkyl, alkoxy, vinyl, 1 E-alkenyl or 3 E-alkenyl, Alkyl or Alkyl* are each, independently of one another, straight-chain alkyl having 1–6 carbon atoms, and L is H or F.

The liquid-crystalline phases according to the invention comprise from about 0.1 to 99%, preferably 10 to 95%, of one or more compounds of the formula I. Additionally preferred liquid-crystalline phases are those which comprise 0.1–50%, particularly 0.5–30%, of one or more compounds of the formula I. Isotropic compounds of the formula I can also be used in the phases according to the invention.

The liquid-crystalline phases according to the invention are prepared in a manner which is customary per se. In general, the components are dissolved in one another, expediently at elevated temperature.

By means of suitable additives, the liquid-crystalline phases according to the invention can be modified in a manner such that they can be used in all types of liquid-crystal display elements which have been disclosed hitherto. Additives of this type are known to those skilled in the art and are described in detail in the literature. For example, conductive salts, preferably ethyldimethyldodecylammonium 4-hexyloxybenzoate, tetrabutylammonium tetraphenylborate or complex salts of crown ethers (cf., for example, I. Haller et al., Mol. Cryst. Liq. Cryst. Volume 24, pages 249–258 (1973)) can be added in order to improve the conductivity, dichroic dyes can be added to produce coloured guest-host systems or substances can be added to modify the dielectric anisotropy, the viscosity and/or the orientation of the nematic phases. Substances of this type are described, for example, in DE-A 2,209,127, 2,240,864, 2,321,632, 2,338,281, 2,450,088, 2,637,430, 2,853,728 and 2,902,177.

In the present application and in the examples below, the structures of the liquid-crystal compounds are indicated by means of acronyms, the transformation into chemical formulae taking place in accordance with Tables A and B below. All radicals $C_nH_{2n+1}$ and $C_mH_{2m+1}$ are straight-chain alkyl radicals containing n or m carbon atoms respectively. The coding in Table B is self-evident. In Table A, only the acronym for the parent structure is given. In each individual case, the acronym for the parent structure is followed, separated by a hyphen, by a code for the substituents $R^1$, $R^2$, $L^1$ and $L^2$:

| Code for $R^1$, $R^2$, $L^1$, $L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | F | H |
| nF | $C_nH_{2n+1}$ | F | H | H |
| nOF | $OC_nH_{2n+1}$ | F | H | H |
| nCl | $C_nH_{2n+1}$ | Cl | H | H |
| nF.F | $C_nH_{2n+1}$ | F | F | H |
| nF.F.F | $C_nH_{2n+1}$ | F | F | F |
| nCF$_3$ | $C_nH_{2n+1}$ | CF$_3$ | H | H |
| nOCF$_3$ | $C_nH_{2n+1}$ | OCF$_3$ | H | H |
| nOCF$_2$ | $C_nH_{2n+1}$ | OCHF$_2$ | H | H |
| nS | $C_nH_{2n+1}$ | NCS | H | H |
| rVsN | $C_rH_{2r+1}$—CH=CH—$C_sH_{2s}$— | CN | H | H |
| rEsN | $C_rH_{2r+1}$—O—$C_2H_{2s}$— | CN | H | H |
| nAm | $C_nH_{2n+1}$ | COOC$_m$H$_{2m+1}$ | H | H |

Tables A and B show preferred mixture components in the liquid-crystalline mixtures according to the invention.

TABLE A
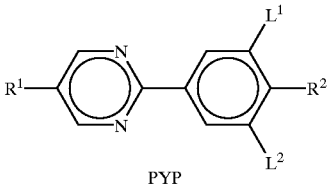
PYP
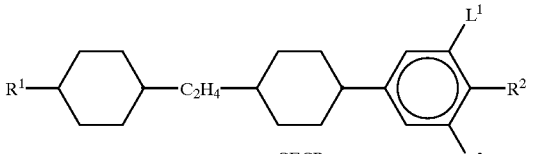
BCH
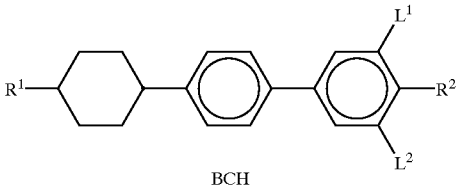
CCH
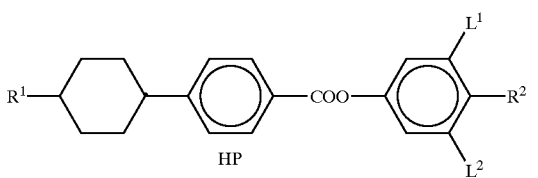
PYRP
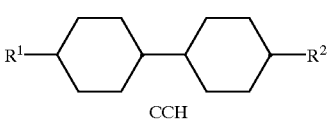
CBC
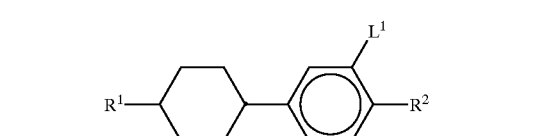
CCP
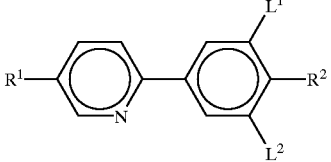
CP
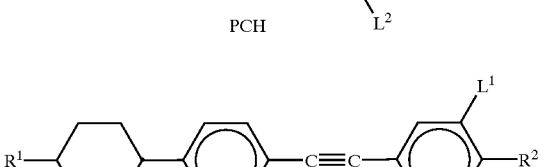
CEPTP
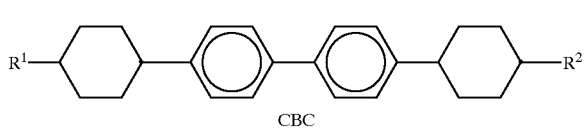
D
TABLE A-continued
CECP
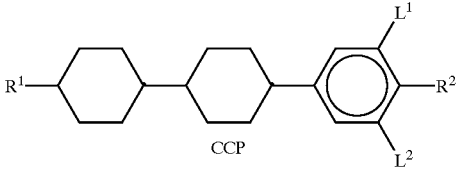
HP
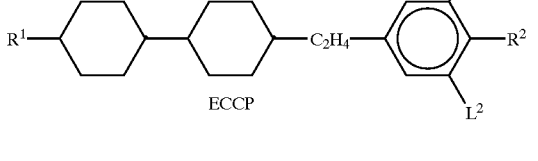
PCH
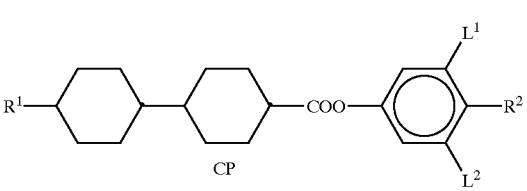
CPTP
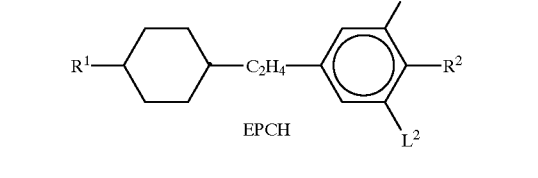
ECCP
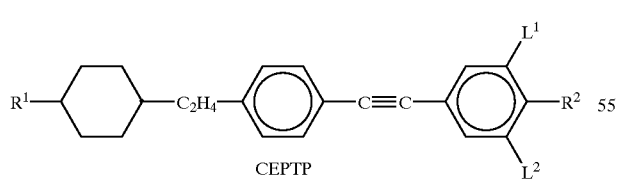
EPCH
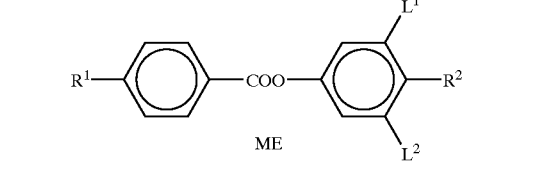
ME
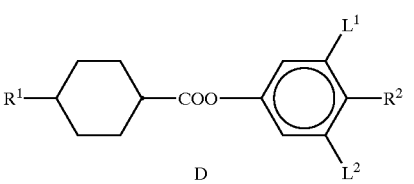
PDX TABLE A-continued
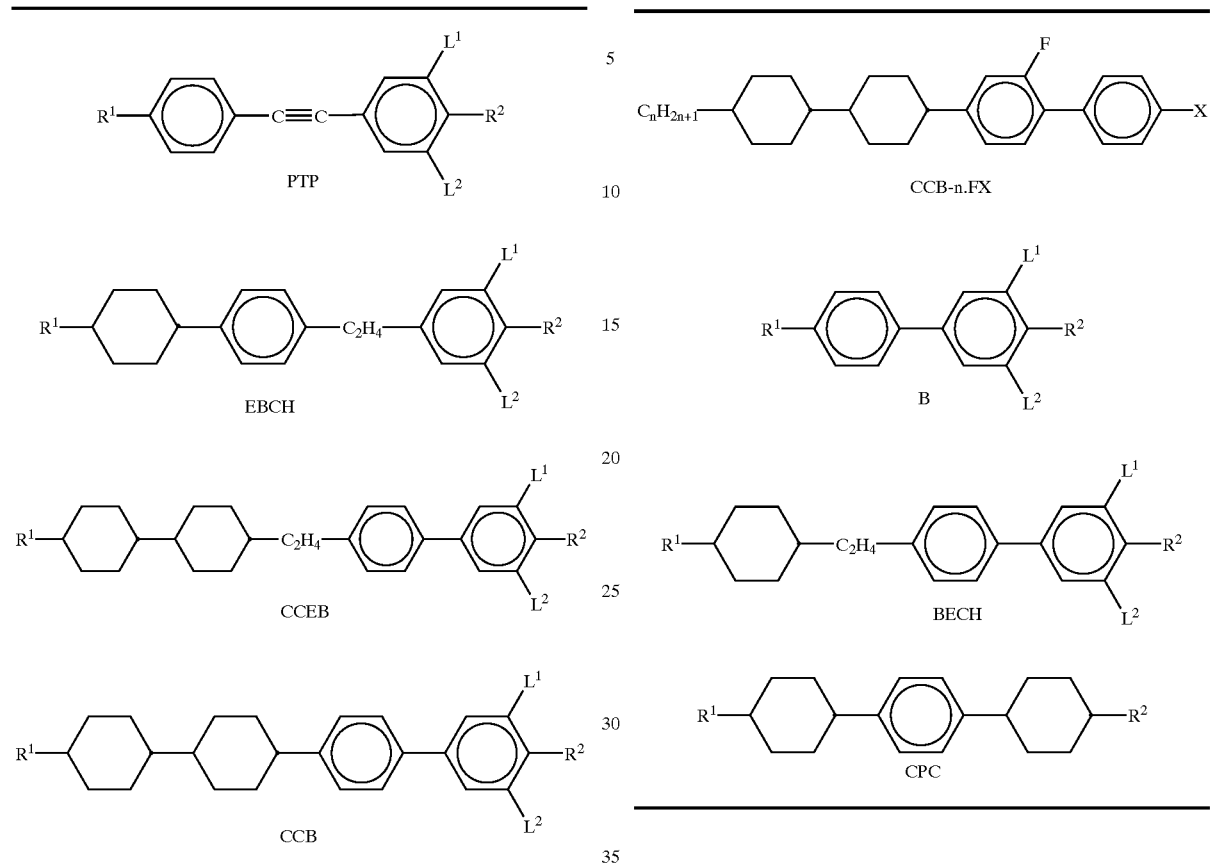
TABLE B
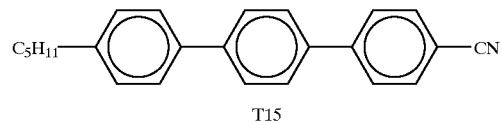
T15
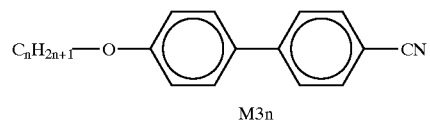
M3n
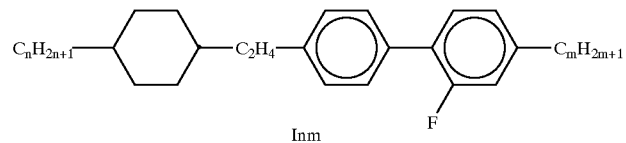
Inm
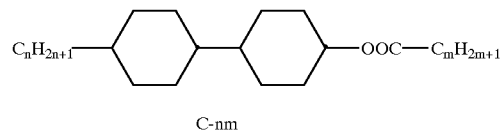
C-nm TABLE B-continued
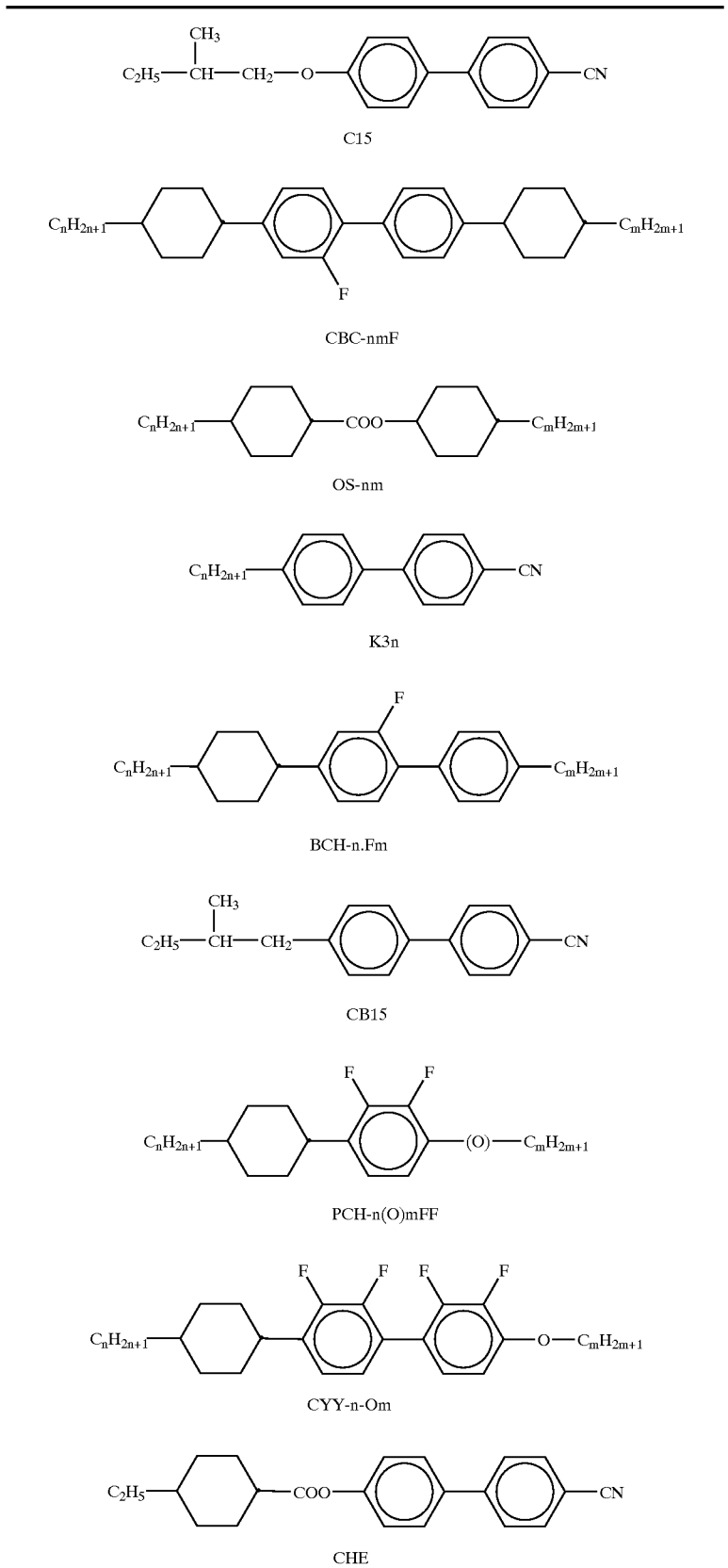

TABLE B-continued
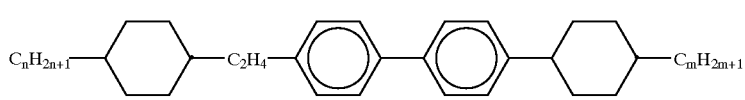
ECBC-nm
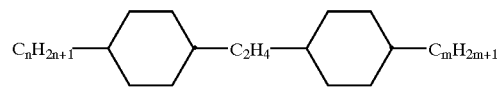
ECCH-nm
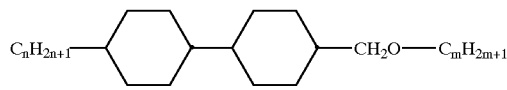
CCH-n1EM
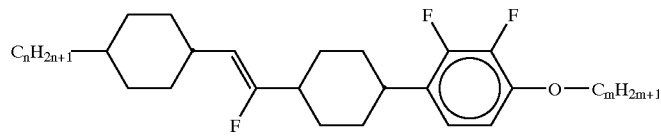
C-0VF-CY-n-Om
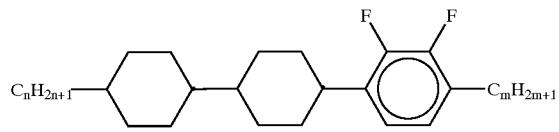
CCP-nmFF
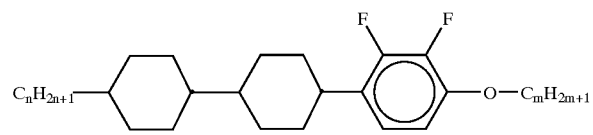
CCP-nOmFF
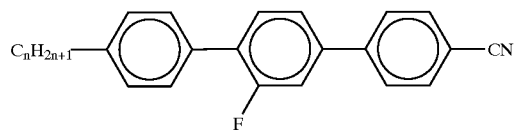
T-nFN
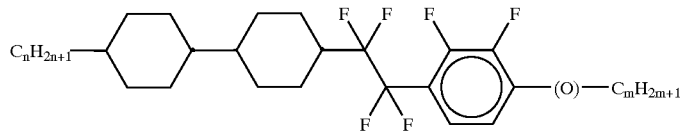
CC—CF$_2$CF$_2$—Y-n(O)m TABLE B-continued

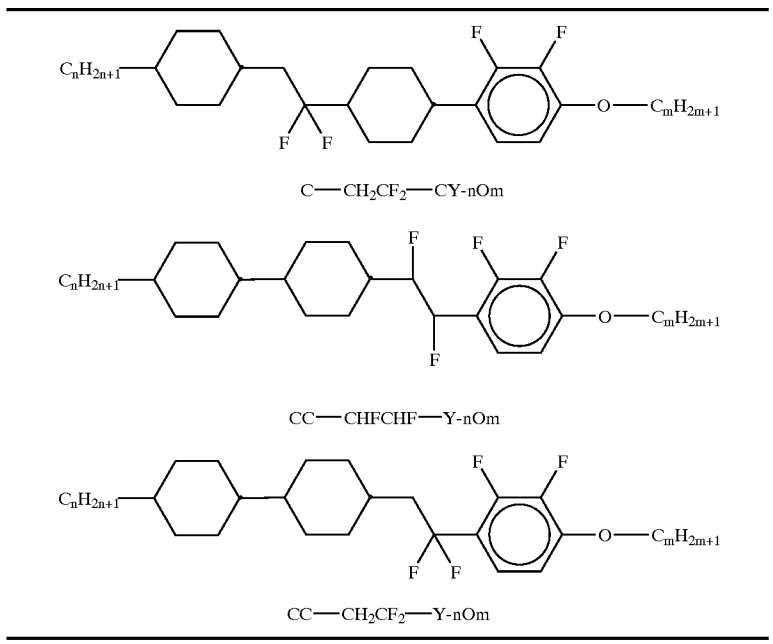

Particularly preferred mixtures according to the invention, in particular for TFT-ECB applications, comprise, besides one or more compounds of the formula I, one, two, three or four compounds of the formula PCH-nmFF, PCH-nOmFF, CCP-nmFF and/or CCP-nOmFF. Preference is furthermore given to mixtures which comprise, besides one or more compounds of the formula I, one, two, three or four neutral compounds of the formula PCH and/or CCH in which $R^1$ and/or $R^2$ are alkyl or alkoxy having 1 to 5 carbon atoms.

The examples below are intended to illustrate the invention without representing a limitation. Above and below, percentages are per cent by weight. All temperatures are given in degrees Celsius. m.p. denotes melting point, cl.p.= clearing point. Furthermore, C=crystalline state, N=nematic phase, S=smectic phase and I=isotropic phase. The figures between these symbols are the transition temperatures. An denotes the optical anisotropy (589 nm, 20° C.), and the viscosity (mm²/sec) was determined at 20° C.

"Conventional work-up" means that water is added if necessary, the mixture is extracted with dichloromethane, diethyl ether, methyl tert-butyl ether or toluene, the organic phase is separated off, dried and evaporated, and the product is purified by distillation under reduced pressure or crystallization and/or chromatography. The following abbreviations are used:

BuLi Butyllithium
DAST Diethylaminosulfur trifluoride
DCC Dicyclohexylcarbodiimide
DDQ Dichlorodicyanobenzoquinone
DIBALH Diisobutylaluminium hydride
KOT Potassium tertiary-butoxide
THF Tetrahydrofuran
pTsOH p-Toluenesulfonic acid
TMEDA Tetramethylethylenediamine
MOST Morpholinosulfur trifluoride

EXAMPLE 1

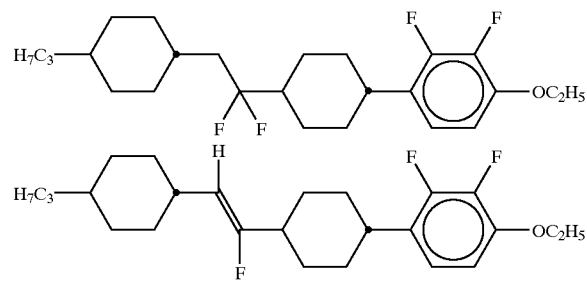

Step 1.1

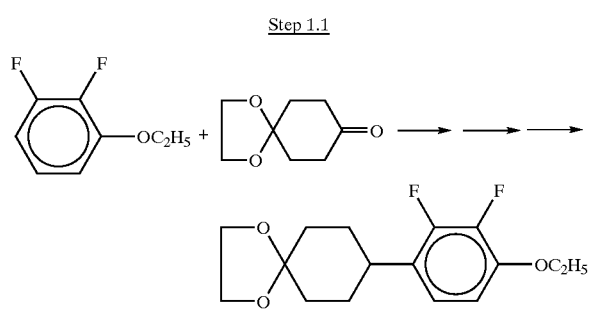

1.1 mol of BuLi (15% solution in n-hexane) are added dropwise under a nitrogen atmosphere at from −70 to −65° C. with stirring to 1 mol of 2,3-difluoroethoxybenzene in 2.5 1 of THF. The mixture is stirred at −70° C. for a further 1 h, and 1 mol of 1,4-cyclohexanedione monoethylene ketone in 500 ml of THF is added dropwise to the solution. The mixture is stirred for a further hour, and the solution is then allowed to warm to −10° C. After 300 ml of water have been added, the solution is adjusted to pH=5–6 using dilute hydrochloric acid. After methyl tert-butyl ether has been added, the organic phase is separated off and subjected to conventional work-up. 1 mol of the crude product is dissolved in 1.5 of toluene, 0.074 mol of p-toluenesulfonic acid is added, and the mixture is stirred overnight at the boil on a water separater.

The solution is allowed to cool to room temperature, 1.788 mol of ethylene glycol are added, and the mixture is refluxed for a further 4 h. The reaction mixture is then allowed to cool to room temperature and subjected to conventional work-up.

0.425 mol of the crude product is hydrogenated in an autoclave at 5 bar and 3° C. with 56 g of Raney nickel.

When the hydrogenation is complete, the reaction mixture is evaporated and crystallized from ethanol.

Step 1.2

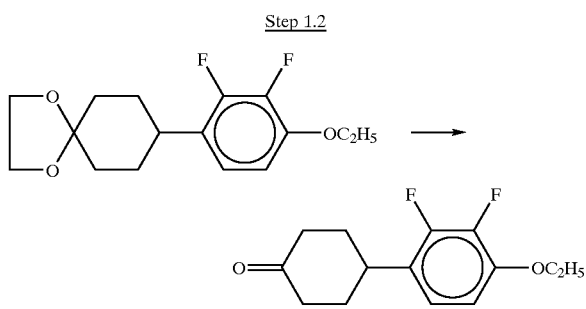

The two-phase mixture consisting of 0.221 mol, 300 ml of formic acid and 600 ml of toluene is stirred overnight under a nitrogen atmosphere. After addition of water, the mixture is subjected to conventional work-up.

Step 1.3

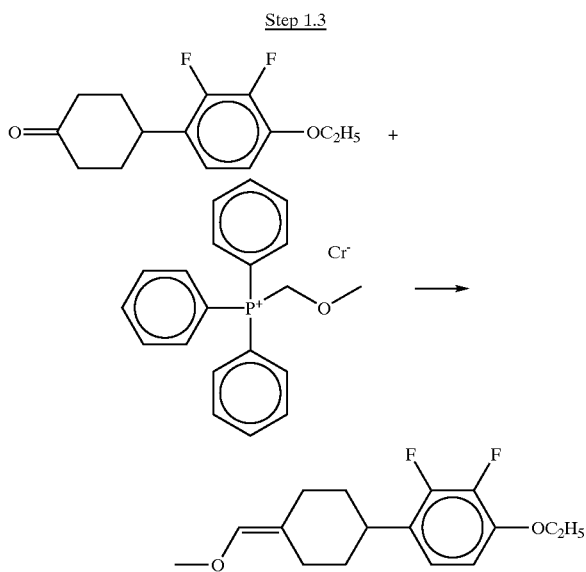

A solution of 15.7 g of potassium tert-butoxide in 100 ml of THF is added dropwise at 0° C. with stirring under a nitrogen atmosphere to 0.140 mol of methoxymethyltriphenylphosphonium chloride in 300 ml of abs. THF. The dark-red ylide is stirred for a further 1 h, and 0.129 mol of ketone from Step 1.2 in 100 ml of THF is added. The reaction mixture is stirred overnight at room temperature, then hydrolysed at 0° C. and adjusted to pH=5–7 using dilute hydrochloric acid. After methyl tert-butyl ether has been added, the mixture is objected to conventional work-up.

Step 1.4

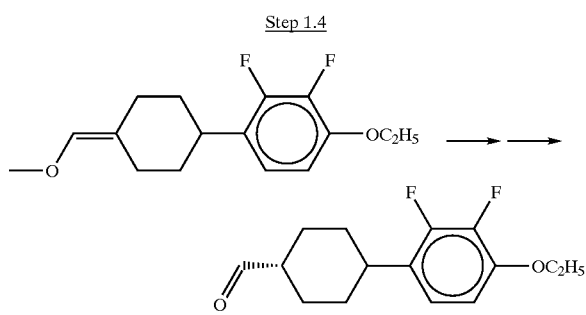

0.078 mol of the ethyl ether from Step 1.3 in 200 ml of toluene and 100 ml of formic acid are stirred overnight at room temperature under a nitrogen atmosphere. After water has been added, the mixture is subjected to conventional work-up. For the isomerization, 0.093 mol of the crude product is dissolved in 300 ml of methanol and 15 ml of 20% sodium hydroxide solution and stirred at room temperature for 2 h. The reaction mixture is evaporated, and NH$_4$Cl solution and methyl tert-butyl ether are added. The mixture is subjected to conventional work-up, and the trans-aldehyde is finally crystallized from n-heptane.

Step 1.5

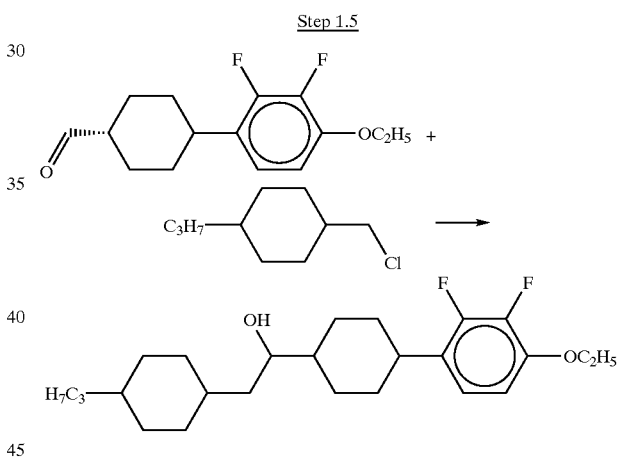

0.377 mol of

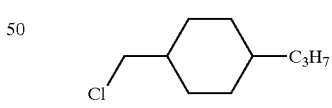

in 100 ml of THF is added dropwise at −10° C. to 0.377 mol of lithium powder in 50 ml of THF, and the mixture is treated with ultrasound at about 0° C. for 2 h. The reaction mixture is cooled to −75° C., and 0.25 mol of the trans-aldehyde from Step 1.4 in 250 ml of THF is added at such a rate that the temperature does not exceed −7° C.

The reaction mixture is allowed to slowly warm to 0° C., 5 ml of methanol are added in order to destroy the excess lithium, and the mixture is hydrolysed using ammonium chloride solution. Finally, the mixture is subjected to conventional work-up.

Step 1.6

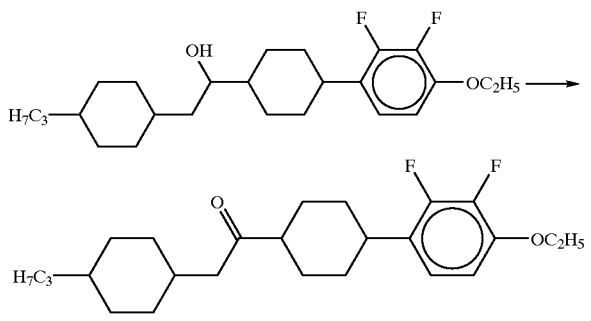

0.044 mol of Jones reagent is added dropwise to 0.044 mol of the alcohol from Step 1.5 in 100 ml of acetone, during which the temperature should not exceed 25° C. The mixture is subsequently stirred for a further 1 h. After isopropanol and water have been added, the mixture is extracted with dichloromethane. Finally, the mixture is subjected to conventional work-up. The crude product is chromatographed on a silica gel column (toluene/ethyl acetate=9:1) and finally recrystallized from ethanol.

Step 1.7

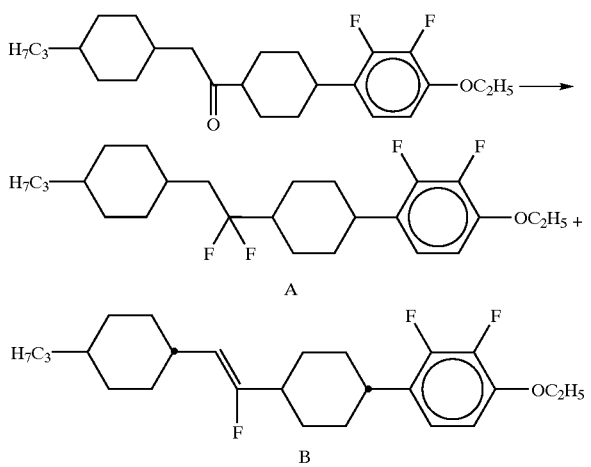

5 g of MOST are added to 0.06 mol of ketone, and the mixture is stirred overnight at 100° C. The reaction mixture is allowed to cool to room temperature, and 30 ml of dichloromethane are added. Water is then added dropwise, and the organic phase is separated off and subjected to conventional work-up. The crude product is firstly eluted on a silica gel frit (hexane/MTB/ether=95:5) and crystallized from ethanol. The vinylene and ethyl compounds are separated by chromatography.

A: C 103 $S_B$ (92) N 134.5 I; $\Delta\epsilon=-6.6$; $\Delta n=+0.100$
B: C 98 $S_B$ (45) N 181.0 I; $\Delta\epsilon=-6.0$
The following compounds of the formula

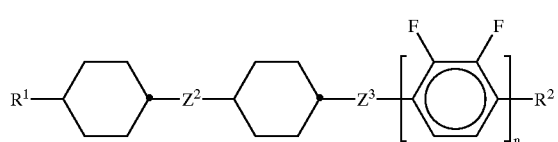

are prepared analogously:

| $R^1$ | $Z^2$ | $Z^3$ | n | $R^2$ |
|---|---|---|---|---|
| $CH_3$ | $-CH_2CF_2-$ | — | 1 | $OCH_3$ |
| $C_2H_5$ | $-CH_2CF_2-$ | — | 1 | $OCH_3$ |
| $n-C_3H_7$ | $-CH_2CF_2-$ | — | 1 | $OCH_3$ |
| $n-C_4H_9$ | $-CH_2CF_2-$ | — | 1 | $OCH_3$ |
| $n-C_5H_{11}$ | $-CH_2CF_2-$ | — | 1 | $OCH_3$ |
| $n-C_6H_{13}$ | $-CH_2CF_2-$ | — | 1 | $OCH_3$ |
| $CH_2=CH$ | $-CH_2CF_2-$ | — | 1 | $OCH_3$ |
| $CH_3CH=CH$ | $-CH_2CF_2-$ | — | 1 | $OCH_3$ |
| $C_3H_7-CH=CH$ | $-CH_2CF_2-$ | — | 1 | $OCH_3$ |
| $CH_2=CH-C_2H_4$ | $-CH_2CF_2-$ | — | 1 | $OCH_3$ |
| $CH_3CH=CH-C_2H_4$ | $-CH_2CF_2-$ | — | 1 | $OCH_3$ |
| $CH_3$ | $-CH_2CF_2-$ | — | 1 | $OC_2H_5$ |
| $C_2H_5$ | $-CH_2CF_2-$ | — | 1 | $OC_2H_5$ |
| $n-C_4H_9$ | $-CH_2CF_2-$ | — | 1 | $OC_2H_5$ |
| $n-C_5H_{11}$ | $-CH_2CF_2-$ | — | 1 | $OC_2H_5$ |
| $n-C_6H_{13}$ | $-CH_2CF_2-$ | — | 1 | $OC_2H_5$ |
| $CH_2=CH$ | $-CH_2CF_2-$ | — | 1 | $OC_2H_5$ |
| $CH_3CH=CH$ | $-CH_2CF_2-$ | — | 1 | $OC_2H_5$ |
| $C_3H_7-CH=CH$ | $-CH_2CF_2-$ | — | 1 | $OC_2H_5$ |
| $CH_2=CH-C_2H_4$ | $-CH_2CF_2-$ | — | 1 | $OC_2H_5$ |
| $CH_3CH=CH-C_2H_4$ | $-CH_2CF_2-$ | — | 1 | $OC_2H_5$ |
| $CH_3$ | $-CH_2CF_2-$ | — | 1 | $OC_3H_7-n$ |
| $C_2H_5$ | $-CH_2CF_2-$ | — | 1 | $OC_3H_7-n$ |
| $n-C_3H_7$ | $-CH_2CF_2-$ | — | 1 | $OC_3H_7-n$ |
| $n-C_4H_9$ | $-CH_2CF_2-$ | — | 1 | $OC_3H_7-n$ |
| $n-C_5H_{11}$ | $-CH_2CF_2-$ | — | 1 | $OC_3H_7-n$ |
| $n-C_6H_{13}$ | $-CH_2CF_2-$ | — | 1 | $OC_3H_7-n$ |
| $CH_2=CH$ | $-CH_2CF_2-$ | — | 1 | $OC_3H_7-n$ |
| $CH_3CH=CH$ | $-CH_2CF_2-$ | — | 1 | $OC_3H_7-n$ |
| $C_3H_7-CH=CH$ | $-CH_2CF_2-$ | — | 1 | $OC_3H_7-n$ |
| $CH_2=CH-C_2H_4$ | $-CH_2CF_2-$ | — | 1 | $OC_3H_7-n$ |
| $CH_3CH=CH-C_2H_4$ | $-CH_2CF_2-$ | — | 1 | $OC_3H_7-n$ |
| $CH_3$ | $-CH_2CF_2-$ | — | 1 | $CH_3$ |
| $C_2H_5$ | $-CH_2CF_2-$ | — | 1 | $CH_3$ |
| $n-C_3H_7$ | $-CH_2CF_2-$ | — | 1 | $CH_3$ |
| $n-C_4H_9$ | $-CH_2CF_2-$ | — | 1 | $CH_3$ |
| $n-C_5H_{11}$ | $-CH_2CF_2-$ | — | 1 | $CH_3$ |
| $n-C_6H_{13}$ | $-CH_2CF_2-$ | — | 1 | $CH_3$ |
| $CH_2=CH$ | $-CH_2CF_2-$ | — | 1 | $CH_3$ |
| $CH_3CH=CH$ | $-CH_2CF_2-$ | — | 1 | $CH_3$ |
| $C_3H_7-CH=CH$ | $-CH_2CF_2-$ | — | 1 | $CH_3$ |
| $CH_2=CH-C_2H_4$ | $-CH_2CF_2-$ | — | 1 | $CH_3$ |
| $CH_3CH=CH-C_2H_4$ | $-CH_2CF_2-$ | — | 1 | $CH_3$ |
| $CH_3$ | $-CH_2CF_2-$ | — | 1 | $C_2H_5$ |
| $C_2H_5$ | $-CH_2CF_2-$ | — | 1 | $C_2H_5$ |
| $n-C_3H_7$ | $-CH_2CF_2-$ | — | 1 | $C_2H_5$ |
| $n-C_4H_9$ | $-CH_2CF_2-$ | — | 1 | $C_2H_5$ |
| $n-C_5H_{11}$ | $-CH_2CF_2-$ | — | 1 | $C_2H_5$ |
| $n-C_6H_{13}$ | $-CH_2CF_2-$ | — | 1 | $C_2H_5$ |
| $CH_2=CH$ | $-CH_2CF_2-$ | — | 1 | $C_2H_5$ |
| $CH_3CH=CH$ | $-CH_2CF_2-$ | — | 1 | $C_2H_5$ |
| $C_3H_7-CH=CH$ | $-CH_2CF_2-$ | — | 1 | $C_2H_5$ |
| $CH_2=CH-C_2H_4$ | $-CH_2CF_2-$ | — | 1 | $C_2H_5$ |
| $CH_3CH=CH-C_2H_4$ | $-CH_2CF_2-$ | — | 1 | $C_2H_5$ |
| $CH_3$ | $-CH_2CF_2-$ | — | 1 | $n-C_3H_7$ |
| $C_2H_5$ | $-CH_2CF_2-$ | — | 1 | $n-C_3H_7$ |
| $n-C_3H_7$ | $-CH_2CF_2-$ | — | 1 | $n-C_3H_7$ |
| $n-C_4H_9$ | $-CH_2CF_2-$ | — | 1 | $n-C_3H_7$ |
| $n-C_5H_{11}$ | $-CH_2CF_2-$ | — | 1 | $n-C_3H_7$ |
| $n-C_6H_{13}$ | $-CH_2CF_2-$ | — | 1 | $n-C_3H_7$ |
| $CH_2=CH$ | $-CH_2CF_2-$ | — | 1 | $n-C_3H_7$ |
| $CH_3CH=CH$ | $-CH_2CF_2-$ | — | 1 | $n-C_3H_7$ |
| $C_3H_7-CH=CH$ | $-CH_2CF_2-$ | — | 1 | $n-C_3H_7$ |
| $CH_2=CH-C_2H_4$ | $-CH_2CF_2-$ | — | 1 | $n-C_3H_7$ |
| $CH_3CH=CH-C_2H_4$ | $-CH_2CF_2-$ | — | 1 | $n-C_3H_7$ |
| $CH_3$ | $-CHFCHF-$ | — | 1 | $OCH_3$ |
| $C_2H_5$ | $-CHFCHF-$ | — | 1 | $OCH_3$ |
| $n-C_3H_7$ | $-CHFCHF-$ | — | 1 | $OCH_3$ |
| $n-C_4H_9$ | $-CHFCHF-$ | — | 1 | $OCH_3$ |
| $n-C_5H_{11}$ | $-CHFCHF-$ | — | 1 | $OCH_3$ |
| $n-C_6H_{13}$ | $-CHFCHF-$ | — | 1 | $OCH_3$ |
| $CH_2=CH$ | $-CHFCHF-$ | — | 1 | $OCH_3$ |
| $CH_3CH=CH$ | $-CHFCHF-$ | — | 1 | $OCH_3$ |
| $C_3H_7-CH=CH$ | $-CHFCHF-$ | — | 1 | $OCH_3$ |
| $CH_2=CH-C_2H_4$ | $-CHFCHF-$ | — | 1 | $OCH_3$ |

| R¹ | Z² | Z³ | n | R² |
|---|---|---|---|---|
| CH₃CH=CH—C₂H₄ | —CHFCHF— | — | 1 | OCH₃ |
| CH₃ | —CHFCHF— | — | 1 | OC₂H₅ |
| C₂H₅ | —CHFCHF— | — | 1 | OC₂H₅ |
| n-C₃H₇ | —CHFCHF— | — | 1 | OC₂H₅ |
| n-C₄H₉ | —CHFCHF— | — | 1 | OC₂H₅ |
| n-C₅H₁₁ | —CHFCHF— | — | 1 | OC₂H₅ |
| n-C₆H₁₃ | —CHFCHF— | — | 1 | OC₂H₅ |
| CH₂=CH | —CHFCHF— | — | 1 | OC₂H₅ |
| CH₃CH=CH | —CHFCHF— | — | 1 | OC₂H₅ |
| C₃H₇—CH=CH | —CHFCHF— | — | 1 | OC₂H₅ |
| CH₂=CH—C₂H₄ | —CHFCHF— | — | 1 | OC₂H₅ |
| CH₃CH=CH—C₂H₄ | —CHFCHF— | — | 1 | OC₂H₅ |
| CH₃ | —CHFCHF— | — | 1 | OC₃H₇-n |
| C₂H₅ | —CHFCHF— | — | 1 | OC₃H₇-n |
| n-C₃H₇ | —CHFCHF— | — | 1 | OC₃H₇-n |
| n-C₄H₉ | —CHFCHF— | — | 1 | OC₃H₇-n |
| n-C₅H₁₁ | —CHFCHF— | — | 1 | OC₃H₇-n |
| n-C₆H₁₃ | —CHFCHF— | — | 1 | OC₃H₇-n |
| CH₂=CH | —CHFCHF— | — | 1 | OC₃H₇-n |
| CH₃CH=CH | —CKFCHF— | — | 1 | OC₃H₇-n |
| C₃H₇—CH=CH | —CHFCHF— | — | 1 | OC₃H₇-n |
| CH₂=CH—C₂H₄ | —CHFCHF— | — | 1 | OC₃H₇-n |
| CH₃CH=CH—C₂H₄ | —CHFCHF— | — | 1 | OC₃H₇-n |
| CH₃ | —CH₂CF₂— | — | 2 | CH₃ |
| C₂H₅ | —CH₂CF₂— | — | 2 | CH₃ |
| n-C₃H₇ | —CH₂CF₂— | — | 2 | CH₃ |
| n-C₄H₉ | —CH₂CF₂— | — | 2 | CH₃ |
| n-C₅H₁₁ | —CH₂CF₂— | — | 2 | CH₃ |
| n-C₆H₁₃ | —CH₂CF₂— | — | 2 | CH₃ |
| CH₂=CH | —CH₂CF₂— | — | 2 | CH₃ |
| CH₃CH=CH | —CH₂CF₂— | — | 2 | CH₃ |
| C₃H₇—CH=CH | —CH₂CF₂— | — | 2 | CH₃ |
| CH₂=CH—C₂H₄ | —CH₂CF₂— | — | 2 | CH₃ |
| CH₃CH=CH—C₂H₄ | —CH₂CF₂— | — | 2 | CH₃ |
| CH₃ | —CH₂CF₂— | — | 2 | C₂H₅ |
| C₂H₅ | —CH₂CF₂— | — | 2 | C₂H₅ |
| n-C₃H₇ | —CH₂CF₂— | — | 2 | C₂H₅ |
| n-C₄H₉ | —CH₂CF₂— | — | 2 | C₂H₅ |
| n-C₅H₁₁ | —CH₂CF₂— | — | 2 | C₂H₅ |
| n-C₆H₁₃ | —CH₂CF₂— | — | 2 | C₂H₅ |
| CH₂=CH | —CH₂CF₂— | — | 2 | C₂H₅ |
| CH₃CH=CH | —CH₂CF₂— | — | 2 | C₂H₅ |
| C₃H₇—CH=CH | —CH₂CF₂— | — | 2 | C₂H₅ |
| CH₂=CH—C₂H₄ | —CH₂CF₂— | — | 2 | C₂H₅ |
| CH₃CH=CH—C₂H₄ | —CH₂CF₂— | — | 2 | C₂H₅ |
| CH₃ | —CH₂CF₂— | — | 2 | n-C₃H₇ |
| C₂H₅ | —CH₂CF₂— | — | 2 | n-C₃H₇ |
| n-C₃H₇ | —CH₂CF₂— | — | 2 | n-C₃H₇ |
| n-C₄H₉ | —CH₂CF₂— | — | 2 | n-C₃H₇ |
| n-C₅H₁₁ | —CH₂CF₂— | — | 2 | n-C₃H₇ |
| n-C₆H₁₃ | —CH₂CF₂— | — | 2 | n-C₃H₇ |
| CH₂=CH | —CH₂CF₂— | — | 2 | n-C₃H₇ |
| CH₃CH=CH | —CH₂CF₂— | — | 2 | n-C₃H₇ |
| C₃H₇—CH=CH | —CH₂CF₂— | — | 2 | n-C₃H₇ |
| CH₂=CH—C₂H₄ | —CH₂CF₂— | — | 2 | n-C₃H₇ |
| CH₃CH=CH—C₂H₄ | —CH₂CF₂— | — | 2 | n-C₃H₇ |
| CH₃ | —CH=CF— | — | 1 | OCH₃ |
| C₂H₅ | —CH=CF— | — | 1 | OCH₃ |
| n-C₃H₇ | —CH=CF— | — | 1 | OCH₃ |
| n-C₄H₉ | —CH=CF— | — | 1 | OCH₃ |
| n-C₅H₁₁ | —CH=CF— | — | 1 | OCH₃ |
| n-C₆H₁₃ | —CH=CF— | — | 1 | OCH₃ |
| CH₂=CH | —CH=CF— | — | 1 | OCH₃ |
| CH₃CH=CH | —CH=CF— | — | 1 | OCH₃ |
| C₃H₇—CH=CH | —CH=CF— | — | 1 | OCH₃ |
| CH₂=CH—C₂H₄ | —CH=CF— | — | 1 | OCH₃ |
| CH₃CH=CH—C₂H₄ | —CH=CF— | — | 1 | OCH₃ |
| CH₃ | —CH=CF— | — | 1 | OC₂H₅ |
| C₂H₅ | —CH=CF— | — | 1 | OC₂H₅ |
| n-C₃H₇ | —CH=CF— | — | 1 | OC₂H₅ |
| n-C₄H₉ | —CH=CF— | — | 1 | OC₂H₅ |
| n-C₅H₁₁ | —CH=CF— | — | 1 | OC₂H₅ |
| n-C₆H₁₃ | —CH=CF— | — | 1 | OC₂H₅ |
| CH₂=CH | —CH=CF— | — | 1 | OC₂H₅ |
| CH₃CH=CH | —CH=CF— | — | 1 | OC₂H₅ |
| C₃H₇—CH=CH | —CH=CF— | — | 1 | OC₂H₅ |
| CH₂=CH—C₂H₄ | —CH=CF— | — | 1 | OC₂H₅ |
| CH₃CH=CH—C₂H₄ | —CH=CF— | — | 1 | OC₂H₅ |
| CH₃ | —CH=CF— | — | 1 | OC₃H₇-n |
| C₂H₅ | —CH=CF— | — | 1 | OC₃H₇-n |
| n-C₃H₇ | —CH=CF— | — | 1 | OC₃H₇-n |
| n-C₄H₉ | —CH=CF— | — | 1 | OC₃H₇-n |
| n-C₅H₁₁ | —CH=CF— | — | 1 | OC₃H₇-n |
| n-C₆H₁₃ | —CH=CF— | — | 1 | OC₃H₇-n |
| CH₂=CH | —CH=CF— | — | 1 | OC₃H₇-n |
| CH₃CH=CH | —CH=CF— | — | 1 | OC₃H₇-n |
| C₃H₇—CH=CH | —CH=CF— | — | 1 | OC₃H₇-n |
| CH₂=CH—C₂H₄ | —CH=CF— | — | 1 | OC₃H₇-n |
| CH₃CH=CH—C₂H₄ | —CH=CF— | — | 1 | OC₃H₇-n |
| CH₃ | —CH=CF— | — | 1 | CH₃ |
| C₂H₅ | —CH=CF— | — | 1 | CH₃ |
| n-C₃H₇ | —CH=CF— | — | 1 | CH₃ |
| n-C₄H₉ | —CH=CF— | — | 1 | CH₃ |
| n-C₅H₁₁ | —CH=CF— | — | 1 | CH₃ |
| n-C₆H₁₃ | —CH=CF— | — | 1 | CH₃ |
| CH₂=CH | —CH=CF— | — | 1 | CH₃ |
| CH₃CH=CH | —CH=CF— | — | 1 | CH₃ |
| C₃H₇—CH=CH | —CH=CF— | — | 1 | CH₃ |
| CH₂=CH—C₂H₄ | —CH=CF— | — | 1 | CH₃ |
| CH₃CH=CH—C₂H₄ | —CH=CF— | — | 1 | CH₃ |
| CH₃ | —CH=CF— | — | 1 | C₂H₅ |
| C₂H₅ | —CH=CF— | — | 1 | C₂H₅ |
| n-C₃H₇ | —CH=CF— | — | 1 | C₂H₅ |
| n-C₄H₉ | —CH=CF— | — | 1 | C₂H₅ |
| n-C₅H₁₁ | —CH=CF— | — | 1 | C₂H₅ |
| n-C₆H₁₃ | —CH=CF— | — | 1 | C₂H₅ |
| CH₂=CH | —CH=CF— | — | 1 | C₂H₅ |
| CH₃CH=CH | —CH=CF— | — | 1 | C₂H₅ |
| C₃H₇—CH=CH | —CH=CF— | — | 1 | C₂H₅ |
| CH₂=CH—C₂H₄ | —CH=CF— | — | 1 | C₂H₅ |
| CH₃CH=CH—C₂H₄ | —CH=CF— | — | 1 | C₂H₅ |
| CH₃ | —CH=CF— | — | 1 | n-C₃H₇ |
| C₂H₅ | —CH=CF— | — | 1 | n-C₃H₇ |
| n-C₃H₇ | —CH=CF— | — | 1 | n-C₃H₇ |
| n-C₄H₉ | —CH=CF— | — | 1 | n-C₃H₇ |
| n-C₅H₁₁ | —CH=CF— | — | 1 | n-C₃H₇ |
| n-C₆H₁₃ | —CH=CF— | — | 1 | n-C₃H₇ |
| CH₂=CH | —CH=CF— | — | 1 | n-C₃H₇ |
| CH₃CH=CH | —CH=CF— | — | 1 | n-C₃H₇ |
| C₃H₇—CH=CH | —CH=CF— | — | 1 | n-C₃H₇ |
| CH₂=CH—C₂H₄ | —CH=CF— | — | 1 | n-C₃H₇ |
| CH₃CH=CH—C₂H₄ | —CH=CF— | — | 1 | n-C₃H₇ |
| CH₃ | —CH=CF— | — | 2 | OCH₃ |
| C₂H₅ | —CH=CF— | — | 2 | OCH₃ |
| n-C₃H₇ | —CH=CF— | — | 2 | OCH₃ |
| n-C₄H₉ | —CH=CF— | — | 2 | OCH₃ |
| n-C₅H₁₁ | —CH=CF— | — | 2 | OCH₃ |
| n-C₆H₁₃ | —CH=CF— | — | 2 | OCH₃ |
| CH₂=CH | —CH=CF— | — | 2 | OCH₃ |
| CH₃CH=CH | —CH=CF— | — | 2 | OCH₃ |
| C₃H₇—CH=CH | —CH=CF— | — | 2 | OCH₃ |
| CH₂=CH—C₂H₄ | —CH=CF— | — | 2 | OCH₃ |
| CH₃CH=CH—C₂H₄ | —CH=CF— | — | 2 | OCH₃ |
| CH₃ | —CH=CF— | — | 2 | OC₂H₅ |
| C₂H₅ | —CH=CF— | — | 2 | OC₂H₅ |
| n-C₃H₇ | —CH=CF— | — | 2 | OC₂H₅ |
| n-C₄H₉ | —CH=CF— | — | 2 | OC₂H₅ |
| n-C₅H₁₁ | —CH=CF— | — | 2 | OC₂H₅ |
| n-C₆H₁₃ | —CH=CF— | — | 2 | OC₂H₅ |
| CH₂=CH | —CH=CF— | — | 2 | OC₂H₅ |
| CH₃CH=CH | —CH=CF— | — | 2 | OC₂H₅ |
| C₃H₇—CH=CH | —CH=CF— | — | 2 | OC₂H₅ |
| CH₂=CH—C₂H₄ | —CH=CF— | — | 2 | OC₂H₅ |
| CH₃CH=CH—C₂H₄ | —CH=CF— | — | 2 | OC₂H₅ |
| CH₃ | —CH=CF— | — | 2 | OC₃H₇-n |
| C₂H₅ | —CH=CF— | — | 2 | OC₃H₇-n |
| n-C₃H₇ | —CH=CF— | — | 2 | OC₃H₇-n |
| n-C₄H₉ | —CH=CF— | — | 2 | OC₃H₇-n |
| n-C₅H₁₁ | —CH=CF— | — | 2 | OC₃H₇-n |
| n-C₆H₁₃ | —CH=CF— | — | 2 | OC₃H₇-n |
| CH₂=CH | —CH=CF— | — | 2 | OC₃H₇-n |
| CH₃CH=CH | —CH=CF— | — | 2 | OC₃H₇-n |
| C₃H₇—CH=CH | —CH=CF— | — | 2 | OC₃H₇-n |
| CH₂=CH—C₂H₄ | —CH=CF— | — | 2 | OC₃H₇-n |

-continued

| R¹ | Z² | Z³ | n | R² |
|---|---|---|---|---|
| CH₃CH=CH—C₂H₄ | —CH=CF— | — | 2 | OC₃H₇-n |
| CH₃ | —CH=CF— | — | 2 | CH₃ |
| C₂H₅ | —CH=CF— | — | 2 | CH₃ |
| n-C₃H₇ | —CH=CF— | — | 2 | CH₃ |
| n-C₄H₉ | —CH=CF— | — | 2 | CH₃ |
| n-C₅H₁₁ | —CH=CF— | — | 2 | CH₃ |
| n-C₆H₁₃ | —CH=CF— | — | 2 | CH₃ |
| CH₂=CH | —CH=CF— | — | 2 | CH₃ |
| CH₃CH=CH | —CH=CF— | — | 2 | CH₃ |
| C₃H₇—CH=CH | —CH=CF— | — | 2 | CH₃ |
| CH₂=CH—C₂H₄ | —CH=CF— | — | 2 | CH₃ |
| CH₃CH=CH—C₂H₄ | —CH=CF— | — | 2 | CH₃ |
| CH₃ | —CH=CF— | — | 2 | C₂H₅ |
| C₂H₅ | —CH=CF— | — | 2 | C₂H₅ |
| n-C₃H₇ | —CH=CF— | — | 2 | C₂H₅ |
| n-C₄H₉ | —CH=CF— | — | 2 | C₂H₅ |
| n-C₅H₁₁ | —CH=CF— | — | 2 | C₂H₅ |
| n-C₆H₁₃ | —CH=CF— | — | 2 | C₂H₅ |
| CH₂=CH | —CH=CF— | — | 2 | C₂H₅ |
| CH₃CH=CH | —CH=CF— | — | 2 | C₂H₅ |
| C₃H₇—CH=CH | —CH=CF— | — | 2 | C₂H₅ |
| CH₂=CH—C₂H₄ | —CH=CF— | — | 2 | C₂H₅ |
| CH₃CH=CH—C₂H₄ | —CH=CF— | — | 2 | C₂H₅ |
| CH₃ | —CH=CF— | — | 2 | n-C₃H₇ |
| C₂H₅ | —CH=CF— | — | 2 | n-C₃H₇ |
| n-C₃H₇ | —CH=CF— | — | 2 | n-C₃H₇ |
| n-C₄H₉ | —CH=CF— | — | 2 | n-C₃H₇ |
| n-C₅H₁₁ | —CH=CF— | — | 2 | n-C₃H₇ |
| n-C₆H₁₃ | —CH=CF— | — | 2 | n-C₃H₇ |
| CH₂=CH | —CH=CF— | — | 2 | n-C₃H₇ |
| CH₃CH=CH | —CH=CF— | — | 2 | n-C₃H₇ |
| C₃H₇—CH=CH | —CH=CF— | — | 2 | n-C₃H₇ |
| CH₂=CH—C₂H₄ | —CH=CF— | — | 2 | n-C₃H₇ |
| CH₃CH=CH—C₂H₄ | —CH=CF— | — | 2 | n-C₃H₇ |
| CH₃ | —CH₂CF₂— | —CH₂CH₂— | 1 | OCH₃ |
| C₂H₅ | —CH₂CF₂— | —CH₂CH₂— | 1 | OCH₃ |
| n-C₃H₇ | —CH₂CF₂— | —CH₂CH₂— | 1 | OCH₃ |
| n-C₄H₉ | —CH₂CF₂— | —CH₂CH₂— | 1 | OCH₃ |
| n-C₅H₁₁ | —CH₂CF₂— | —CH₂CH₂— | 1 | OCH₃ |
| n-C₆H₁₃ | —CH₂CF₂— | —CH₂CH₂— | 1 | OCH₃ |
| CH₂=CH | —CH₂CF₂— | —CH₂CH₂— | 1 | OCH₃ |
| CH₃CH=CH | —CH₂CF₂— | —CH₂CH₂— | 1 | OCH₃ |
| C₃H₇—CH=CH | —CH₂CF₂— | —CH₂CH₂— | 1 | OCH₃ |
| CH₂=CH—C₂H₄ | —CH₂CF₂— | —CH₂CH₂— | 1 | OCH₃ |
| CH₃CH=CH—C₂H₄ | —CH₂CF₂— | —CH₂CH₂— | 1 | OCH₃ |
| CH₃ | —CH₂CF₂— | —CH₂CH₂— | 1 | OC₂H₅ |
| C₂H₅ | —CH₂CF₂— | —CH₂CH₂— | 1 | OC₂H₅ |
| n-C₄H₉ | —CH₂CF₂— | —CH₂CH₂— | 1 | OC₂H₅ |
| n-C₅H₁₁ | —CH₂CF₂— | —CH₂CH₂— | 1 | OC₂H₅ |
| n-C₆H₁₃ | —CH₂CF₂— | —CH₂CH₂— | 1 | OC₂H₅ |
| CH₂=CH | —CH₂CF₂— | —CH₂CH₂— | 1 | OC₂H₅ |
| CH₃CH=CH | —CH₂CF₂— | —CH₂CH₂— | 1 | OC₂H₅ |
| C₃H₇—CH=CH | —CH₂CF₂— | —CH₂CH₂— | 1 | OC₂H₅ |
| CH₂=CH—C₂H₄ | —CH₂CF₂— | —CH₂CH₂— | 1 | OC₂H₅ |
| CH₃CH=CH—C₂H₄ | —CH₂CF₂— | —CH₂CH₂— | 1 | OC₂H₅ |
| CH₃ | —CH₂CF₂— | —CH₂CH₂— | 1 | OC₃H₇-n |
| C₂H₅ | —CH₂CF₂— | —CH₂CH₂— | 1 | OC₃H₇-n |
| n-C₃H₇ | —CH₂CF₂— | —CH₂CH₂— | 1 | OC₃H₇-n |
| n-C₄H₉ | —CH₂CF₂— | —CH₂CH₂— | 1 | OC₃H₇-n |
| n-C₅H₁₁ | —CH₂CF₂— | —CH₂CH₂— | 1 | OC₃H₇-n |
| n-C₆H₁₃ | —CH₂CF₂— | —CH₂CH₂— | 1 | OC₃H₇-n |
| CH₂=CH | —CH₂CF₂— | —CH₂CH₂— | 1 | OC₃H₇-n |
| CH₃CH=CH | —CH₂CF₂— | —CH₂CH₂— | 1 | OC₃H₇-n |
| C₃H₇—CH=CH | —CH₂CF₂— | —CH₂CH₂— | 1 | OC₃H₇-n |
| CH₂=CH—C₂H₄ | —CH₂CF₂— | —CH₂CH₂— | 1 | OC₃H₇-n |
| CH₃CH=CH—C₂R4 | —CH₂CF₂— | —CH₂CH₂— | 1 | OC₃H₇-n |
| CH₃ | —CH₂CF₂— | —(CH₂)₄— | 1 | CH₃ |
| C₂H₅ | —CH₂CF₂— | —(CH₂)₄— | 1 | CH₃ |
| n-C₃H₇ | —CH₂CF₂— | —(CH₂)₄— | 1 | CH₃ |
| n-C₄H₉ | —CH₂CF₂— | —(CH₂)₄— | 1 | CH₃ |
| n-C₅H₁₁ | —CH₂CF₂— | —(CH₂)₄— | 1 | CH₃ |
| n-C₆H₁₃ | —CH₂CF₂— | —(CH₂)₄— | 1 | CH₃ |
| CH₂=CH | —CH₂CF₂— | —(CH₂)₄— | 1 | CH₃ |
| CH₃CH=CH | —CH₂CF₂— | —(CH₂)₄— | 1 | CH₃ |
| C₃H₇—CH=CH | —CH₂CF₂— | —(CH₂)₄— | 1 | CH₃ |
| CH₂=CH—C₂H₄ | —CH₂CF₂— | —(CH₂)₄— | 1 | CH₃ |
| CH₃CH=CH—C₂H₄ | —CH₂CF₂— | —(CH₂)₄— | 1 | CH₃ |

-continued

| R¹ | Z² | Z³ | n | R² |
|---|---|---|---|---|
| CH₃ | —CH₂CF₂— | —(CH₂)₄— | 1 | C₂H₅ |
| C₂H₅ | —CH₂CF₂— | —(CH₂)₄— | 1 | C₂H₅ |
| n-C₃H₇ | —CH₂CF₂— | —(CH₂)₄— | 1 | C₂H₅ |
| n-C₄H₉ | —CH₂CF₂— | —(CH₂)₄— | 1 | C₂H₅ |
| n-C₅H₁₁ | —CH₂CF₂— | —(CH₂)₄— | 1 | C₂H₅ |
| n-C₆H₁₃ | —CH₂CF₂— | —(CH₂)₄— | 1 | C₂H₅ |
| CH₂=CH | —CH₂CF₂— | —(CH₂)₄— | 1 | C₂H₅ |
| CH₃CH=CH | —CH₂CF₂— | —(CH₂)₄— | 1 | C₂H₅ |
| C₃H₇—CH=CH | —CH₂CF₂— | —(CH₂)₄— | 1 | C₂H₅ |
| CH₂=CH—C₂H₄ | —CH₂CF₂— | —(CH₂)₄— | 1 | C₂H₅ |
| CH₃CH=CH—C₂H₄ | —CH₂CF₂— | —(CH₂)₄— | 1 | C₂H₅ |
| CH₃ | —CH₂CF₂— | —(CH₂)₄— | 1 | n-C₃H₇ |
| C₂H₅ | —CH₂CF₂— | —(CH₂)₄— | 1 | n-C₃H₇ |
| n-C₃H₇ | —CH₂CF₂— | —(CH₂)₄— | 1 | n-C₃H₇ |
| n-C₄H₉ | —CH₂CF₂— | —(CH₂)₄— | 1 | n-C₃H₇ |
| n-C₅H₁₁ | —CH₂CF₂— | —(CH₂)₄— | 1 | n-C₃H₇ |
| n-C₆H₁₃ | —CH₂CF₂— | —(CH₂)₄— | 1 | n-C₃H₇ |
| CH₂=CH | —CH₂CF₂— | —(CH₂)₄— | 1 | n-C₃H₇ |
| CH₃CH=CH | —CH₂CF₂— | —(CH₂)₄— | 1 | n-C₃H₇ |
| C₃H₇—CH=CH | —CH₂CF₂— | —(CH₂)₄— | 1 | n-C₃H₇ |
| CH₂=CH—C₂H₄ | —CH₂CF₂— | —(CH₂)₄— | 1 | n-C₃H₇ |
| CH₃CH=CH—C₂H₄ | —CH₂CF₂— | —(CH₂)₄— | 1 | n-C₃H₇ |
| CH₃ | —CH₂CF₂— | —CH₂O— | 2 | OCH₃ |
| C₂H₅ | —CH₂CF₂— | —CH₂O— | 2 | OCH₃ |
| n-C₃H₇ | —CH₂CF₂— | —CH₂O— | 2 | OCH₃ |
| n-C₄H₉ | —CH₂CF₂— | —CH₂O— | 2 | OCH₃ |
| n-C₅H₁₁ | —CH₂CF₂— | —CH₂O— | 2 | OCH₃ |
| n-C₆H₁₃ | —CH₂CF₂— | —CH₂O— | 2 | OCH₃ |
| CH₂=CH | —CH₂CF₂— | —CH₂O— | 2 | OCH₃ |
| CH₃CH=CH | —CH₂CF₂— | —CH₂O— | 2 | OCH₃ |
| C₃H₇—CH=CH | —CH₂CF₂— | —CH₂O— | 2 | OCH₃ |
| CH₂=CH—C₂H₄ | —CH₂CF₂— | —CH₂O— | 2 | OCH₃ |
| CH₃CH=CH—C₂H₄ | —CH₂CF₂— | —CH₂O— | 2 | OCH₃ |
| CH₃ | —CH₂CF₂— | —CH₂O— | 2 | OC₂H₅ |
| C₂H₅ | —CH₂CF₂— | —CH₂O— | 2 | OC₂H₅ |
| n-C₃H₇ | —CH₂CF₂— | —CH₂O— | 2 | OC₂H₅ |
| n-C₄H₉ | —CH₂CF₂— | —CH₂O— | 2 | OC₂H₅ |
| n-C₅H₁₁ | —CH₂CF₂— | —CH₂O— | 2 | OC₂H₅ |
| n-C₆H₁₃ | —CH₂CF₂— | —CH₂O— | 2 | OC₂H₅ |
| CH₂=CH | —CH₂CF₂— | —CH₂O— | 2 | OC₂H₅ |
| CH₃CH=CH | —CH₂CF₂— | —CH₂O— | 2 | OC₂H₅ |
| C₃H₇—CH=CH | —CH₂CF₂— | —CH₂O— | 2 | OC₂H₅ |
| CH₂=CH—C₂H₄ | —CH₂CF₂— | —CH₂O— | 2 | OC₂H₅ |
| CH₃CH=CH—C₂H₄ | —CH₂CF₂— | —CH₂O— | 2 | OC₂H₅ |
| CH₃ | —CH₂CF₂— | —CH₂O— | 2 | OC₃H₇-n |
| C₂H₅ | —CH₂CF₂— | —CH₂O— | 2 | OC₃H₇-n |
| n-C₃H₇ | —CH₂CF₂— | —CH₂O— | 2 | OC₃H₇-n |
| n-C₄H₉ | —CH₂CF₂— | —CH₂O— | 2 | OC₃H₇-n |
| n-C₅H₁₁ | —CH₂CF₂— | —CH₂O— | 2 | OC₃H₇-n |
| n-C₆H₁₃ | —CH₂CF₂— | —CH₂O— | 2 | OC₃H₇-n |
| CH₂=CH | —CH₂CF₂— | —CH₂O— | 2 | OC₃H₇-n |
| CH₃CH=CH | —CH₂CF₂— | —CH₂O— | 2 | OC₃H₇-n |
| C₃H₇—CH=CH | —CH₂CF₂— | —CH₂O— | 2 | OC₃H₇-n |
| CH₂=CH—C₂H₄ | —CH₂CF₂— | —CH₂O— | 2 | OC₃H₇-n |
| CH₃CH=CH—C₂H₄ | —CH₂CF₂— | —CH₂O— | 2 | OC₃H₇-n |
| CH₃ | —CH₂CF₂— | — | 1 | OCH₃ |
| C₂H₅ | —CH₂CF₂— | — | 1 | OCH₃ |
| n-C₃H₇ | —CH₂CF₂— | — | 1 | OCH₃ |
| n-C₄H₉ | —CH₂CF₂— | — | 1 | OCH₃ |
| n-C₅H₁₁ | —CH₂CF₂— | — | 1 | OCH₃ |
| n-C₆H₁₃ | —CH₂CF₂— | — | 1 | OCH₃ |
| CH₂=CH | —CH₂CF₂— | — | 1 | OCH₃ |
| CH₃CH=CH | —CH₂CF₂— | — | 1 | OCH₃ |
| C₃H₇—CH=CH | —CH₂CF₂— | — | 1 | OCH₃ |
| CH₂=CH—C₂H₄ | —CH₂CF₂— | — | 1 | OCH₃ |
| CH₃CH=CH—C₂H₄ | —CH₂CF₂— | — | 1 | OCH₃ |
| CH₃ | —CH₂CF₂— | — | 1 | OC₂H₅ |
| C₂H₅ | —CH₂CF₂— | — | 1 | OC₂H₅ |
| n-C₃H₇ | —CH₂CF₂— | — | 1 | OC₂H₅ |
| n-C₄H₉ | —CH₂CF₂— | — | 1 | OC₂H₅ |
| n-C₅H₁₁ | —CH₂CF₂— | — | 1 | OC₂H₅ |
| n-C₆H₁₃ | —CH₂CF₂— | — | 1 | OC₂H₅ |
| CH₂=CH | —CH₂CF₂— | — | 1 | OC₂H₅ |
| CH₃CH=CH | —CH₂CF₂— | — | 1 | OC₂H₅ |
| C₃H₇—CH=CH | —CH₂CF₂— | — | 1 | OC₂H₅ |
| CH₂=CH—C₂H₄ | —CH₂CF₂— | — | 1 | OC₂H₅ |
| CH₃CH=CH—C₂H₄ | —CH₂CF₂— | — | 1 | OC₂H₅ |

-continued

| R¹ | Z² | Z³ | n | R² |
|---|---|---|---|---|
| CH₃ | —CH₂CF₂— | — | 2 | n-C₃H₇ |
| C₂H₅ | —CH₂CF₂— | — | 2 | n-C₃H₇ |
| n-C₃H₇ | —CH₂CF₂— | — | 2 | n-C₃H₇ |
| n-C₄H₉ | —CH₂CF₂— | — | 2 | n-C₃H₇ |
| n-C₅H₁₁ | —CH₂CF₂— | — | 2 | n-C₃H₇ |
| n-C₆H₁₃ | —CH₂CF₂— | — | 2 | n-C₃H₇ |
| CH₂=CH | —CH₂CF₂— | — | 2 | n-C₃H₇ |
| CH₃CH=CH | —CH₂CF₂— | — | 2 | n-C₃H₇ |
| C₃H₇—CH=CH | —CH₂CF₂— | — | 2 | n-C₃H₇ |
| CH₂=CH—C₂H₄ | —CH₂CF₂— | — | 2 | n-C₃H₇ |
| CH₃CH=CH—C₂H₄ | —CH₂CF₂— | — | 2 | n-C₃H₇ |

EXAMPLE 2

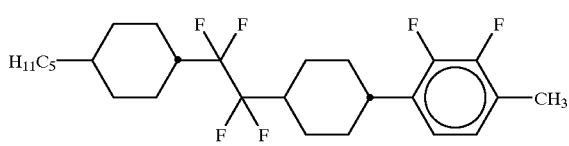

Step 2.1

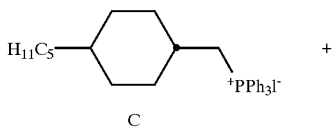

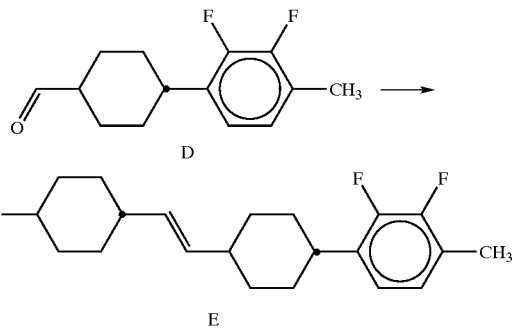

0.250 mol of C are suspended at 0° C. in 350 ml of abs. THF under a nitrogen atmosphere. After addition of 0.250 mol of potassium tert-butoxide, a solution consisting of 0.250 mol of D in 80 ml of abs. THF is added dropwise at 0° C. The mixture is allowed to warm to room temperature and left to stir overnight. After addition of 500 ml of water, the pH of the suspension is adjusted to 3–4 using conc. HCl. Finally, the mixture is subjected to conventional work-up.

Step 2.2

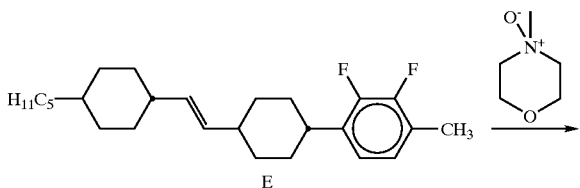

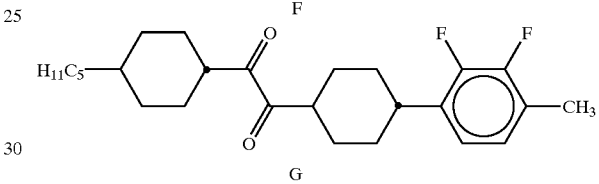

0.125 mol of E, 0.138 mol of N-methylmorpholine N-oxide, 57 ml of H₂O, 0.339 mmol of osmium(VIII) oxide (4% in H₂O) and 500 mol of 1,4-dioxane are heated to the boil with stirring and refluxed overnight. After cooling to room temperature, the solution is evaporated in a rotary evaporator, and the residue is recrystallized from acetone.

Step 2.3

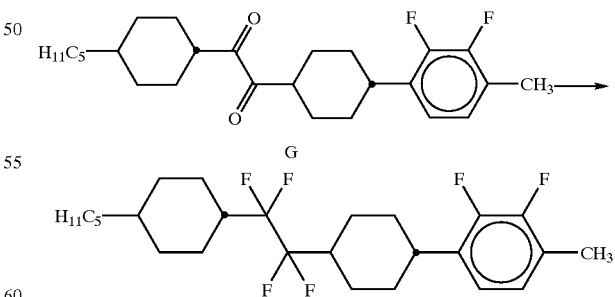

293.7 mmol of trifluoroacetic anhydride are added dropwise at −60° C. to 1.71 mol of dimethyl sulfoxide in 600 ml of dichloromethane under a nitrogen atmosphere. The mixture is left to stir at −60° C. for 10 minutes, and a solution consisting of 97.6 mmol of F in 63 ml of dimethyl sulfoxide, 70 ml of dichloromethane and 70 ml of THF is then added dropwise. The mixture is stirred at −60° C. for 1 hour, and 91.7 ml of triethylamine are added. After the reaction is complete, the mixture is stirred at −6° C. for a further 0.5 hour. The mixture is allowed to warm to 5° C., 1000 ml of 2 N hydrochloric acid are added, and the mixture is subjected to conventional work-up.

Step 2.4

The diketone G is converted into the —C₂F₄— compound as described in J. Am. Chem. Soc. 88, 2796–2799 (1966). In an autoclave, 0.03 mol of diketone G in 100 ml of CH₂Cl₂ and 0.17 mol of water are reacted with ~0.3 mol of SF₄. The mixture is subsequently subjected to conventional work-up.

The following compounds of the formula

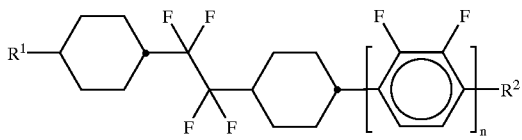

are prepared analogously:

| R¹ | n | R² |
|---|---|---|
| $CH_3$ | 1 | $CH_3$ |
| $C_2H_5$ | 1 | $CH_3$ |
| $n-C_3H_7$ | 1 | $CH_3$ |
| $n-C_4H_9$ | 1 | $CH_3$ |
| $n-C_6H_{13}$ | 1 | $CH_3$ |
| $CH_2=CH$ | 1 | $CH_3$ |
| $CH_3CH=CH$ | 1 | $CH_3$ |
| $C_3H_7-CH=CH$ | 1 | $CH_3$ |
| $CH_2=CH-C_2H_4$ | 1 | $CH_3$ |
| $CH_3$ | 1 | $C_2H_5$ |
| $C_2H_5$ | 1 | $C_2H_5$ |
| $n-C_3H_7$ | 1 | $C_2H_5$ |
| $n-C_4H_9$ | 1 | $C_2H_5$ |
| $n-C_5H_{11}$ | 1 | $C_2H_5$ |
| $n-C_6H_{13}$ | 1 | $C_2H_5$ |
| $CH_2=CH$ | 1 | $C_2H_5$ |
| $CH_3CH=CH$ | 1 | $C_2H_5$ |
| $C_3H_7-CH=CH$ | 1 | $C_2H_5$ |
| $CH_2=CH-C_2H_4$ | 1 | $C_2H_5$ |
| $CH_3$ | 1 | $n-C_3H_7$ |
| $C_2H_5$ | 1 | $n-C_3H_7$ |
| $n-C_3H_7$ | 1 | $n-C_3H_7$ |
| $n-C_4H_9$ | 1 | $n-C_3H_7$ |
| $n-C_5H_{11}$ | 1 | $n-C_3H_7$ |
| $n-C_6H_{13}$ | 1 | $n-C_3H_7$ |
| $CH_2=CH$ | 1 | $n-C_3H_7$ |
| $CH_3CH=CH$ | 1 | $n-C_3H_7$ |
| $C_3H_7-CH=CH$ | 1 | $n-C_3H_7$ |
| $CH_2=CH-C_2H_4$ | 1 | $n-C_3H_7$ |
| $CH_3$ | 1 | $OCH_3$ |
| $C_2H_5$ | 1 | $OCH_3$ |
| $n-C_3H_7$ | 1 | $OCH_3$ |
| $n-C_4H_9$ | 1 | $OCH_3$ |
| $n-C_6H_{13}$ | 1 | $OCH_3$ |
| $CH_2=CH$ | 1 | $OCH_3$ |
| $CH_3CH=CH$ | 1 | $OCH_3$ |
| $C_3H_7-CH=CH$ | 1 | $OCH_3$ |
| $CH_2=CH-C_2H_4$ | 1 | $OCH_3$ |
| $CH_3$ | 1 | $OC_2H_5$ |
| $C_2H_5$ | 1 | $OC_2H_5$ |
| $n-C_3H_7$ | 1 | $OC_2H_5$ |
| $n-C_4H_9$ | 1 | $OC_2H_5$ |
| $n-C_5H_{11}$ | 1 | $OC_2H_5$ |
| $n-C_6H_{13}$ | 1 | $OC_2H_5$ |
| $CH_2=CH$ | 1 | $OC_2H_5$ |
| $CH_3CH=CH$ | 1 | $OC_2H_5$ |
| $C_3H_7-CH=CH$ | 1 | $OC_2H_5$ |
| $CH_2=CH-C_2H_4$ | 1 | $OC_2H_5$ |
| $CH_3$ | 1 | $OC_3H_7-n$ |
| $C_2H_5$ | 1 | $OC_3H_7-n$ |
| $n-C_3H_7$ | 1 | $OC_3H_7-n$ |
| $n-C_4H_9$ | 1 | $OC_3H_7-n$ |
| $n-C_5H_{11}$ | 1 | $OC_3H_7-n$ |
| $n-C_6H_{13}$ | 1 | $OC_3H_7-n$ |
| $CH_2=CH$ | 1 | $OC_3H_7-n$ |
| $CH_3CH=CH$ | 1 | $OC_3H_7-n$ |
| $C_3H_7-CH=CH$ | 1 | $OC_3H_7-n$ |
| $CH_2=CH-C_2H_4$ | 1 | $OC_3H_7-n$ |
| $CH_3$ | 2 | $CH_3$ |
| $C_2H_5$ | 2 | $CH_3$ |
| $n-C_3H_7$ | 2 | $CH_3$ |
| $n-C_4H_9$ | 2 | $CH_3$ |
| $n-C_5H_{11}$ | 2 | $CH_3$ |
| $n-C_6H_{13}$ | 2 | $CH_3$ |
| $CH_2=CH$ | 2 | $CH_3$ |
| $CH_3CH=CH$ | 2 | $CH_3$ |
| $C_3H_7-CH=CH$ | 2 | $CH_3$ |
| $CH_2=CH-C_2H_4$ | 2 | $CH_3$ |
| $CH_3$ | 2 | $C_2H_5$ |
| $C_2H_5$ | 2 | $C_2H_5$ |
| $n-C_3H_7$ | 2 | $C_2H_5$ |
| $n-C_4H_9$ | 2 | $C_2H_5$ |
| $n-C_5H_{11}$ | 2 | $C_2H_5$ |
| $n-C_6H_{13}$ | 2 | $C_2H_5$ |
| $CH_2=CH$ | 2 | $C_2H_5$ |
| $CH_3CH=CH$ | 2 | $C_2H_5$ |
| $C_3H_7-CH=CH$ | 2 | $C_2H_5$ |
| $CH_2=CH-C_2H_4$ | 2 | $C_2H_5$ |
| $CH_3$ | 2 | $n-C_3H_7$ |
| $C_2H_5$ | 2 | $n-C_3H_7$ |
| $n-C_3H_7$ | 2 | $n-C_3H_7$ |
| $n-C_4H_9$ | 2 | $n-C_3H_7$ |
| $n-C_5H_{11}$ | 2 | $n-C_3H_7$ |
| $n-C_6H_{13}$ | 2 | $n-C_3H_7$ |
| $CH_2=CH$ | 2 | $n-C_3H_7$ |
| $CH_3CH=CH$ | 2 | $n-C_3H_7$ |
| $C_3H_7-CH=CH$ | 2 | $n-C_3H_7$ |
| $CH_2=CH-C_2H_4$ | 2 | $n-C_3H_7$ |
| $CH_3$ | 2 | $OCH_3$ |
| $C_2H_5$ | 2 | $OCH_3$ |
| $n-C_3H_7$ | 2 | $OCH_3$ |
| $n-C_4H_9$ | 2 | $OCH_3$ |
| $n-C_6H_{13}$ | 2 | $OCH_3$ |
| $CH_2=CH$ | 2 | $OCH_3$ |
| $CH_3CH=CH$ | 2 | $OCH_3$ |
| $C_3H_7-CH=CH$ | 2 | $OCH_3$ |
| $CH_2=CH-C_2H_4$ | 2 | $OCH_3$ |
| $CH_3$ | 2 | $OC_2H_5$ |
| $C_2H_5$ | 2 | $OC_2H_5$ |
| $n-C_3H_7$ | 2 | $OC_2H_5$ |
| $n-C_4H_9$ | 2 | $OC_2H_5$ |
| $n-C_5H_{11}$ | 2 | $OC_2H_5$ |
| $n-C_6H_{13}$ | 2 | $OC_2H_5$ |
| $CH_2=CH$ | 2 | $OC_2H_5$ |
| $CH_3CH=CH$ | 2 | $OC_2H_5$ |
| $C_3H_7-CH=CH$ | 2 | $OC_2H_5$ |
| $CH_2=CH-C_2H_4$ | 2 | $OC_2H_5$ |
| $CH_3$ | 2 | $OC_3H_7-n$ |
| $C_2H_5$ | 2 | $OC_3H_7-n$ |
| $n-C_3H_7$ | 2 | $OC_3H_7-n$ |
| $n-C_4H_9$ | 2 | $OC_3H_7-n$ |
| $n-C_5H_{11}$ | 2 | $OC_3H_7-n$ |
| $n-C_6H_{13}$ | 2 | $OC_3H_7-n$ |
| $CH_2=CH$ | 2 | $OC_3H_7-n$ |
| $CH_3CH=CH$ | 2 | $OC_3H_7-n$ |
| $C_3H_7-CH=CH$ | 2 | $OC_3H_7-n$ |
| $CH_2=CH-C_2H_4$ | 2 | $OC_3H_7-n$ |

EXAMPLE 3

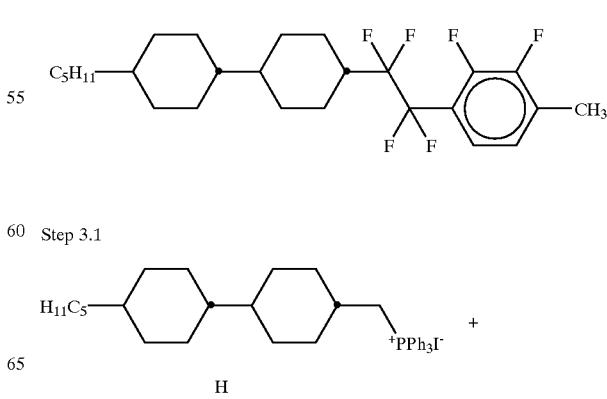

Step 3.1

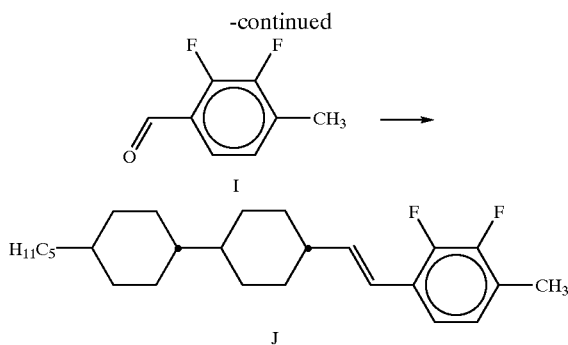

0.250 mol of H are suspended at 0° C. in 350 ml of abs. THF under a nitrogen atmosphere. After addition of 0.250 mol of potassium tert-butoxide, a solution consisting of 0.250 mol of I in 80 ml of abs. THF is added dropwise at 0° C. The mixture is allowed to warm to room temperature and left to stir overnight. After addition of 500 ml of water, the pH of the suspension is adjusted to 3–4 using conc. HCl. Finally, the mixture is subjected to conventional work-up.

Step 3.2

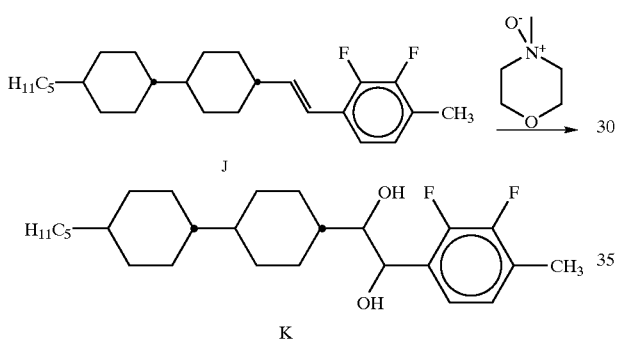

5 0.125 mol of J, 0.138 mol of N-methylmorpholine N-oxide, 57 ml of $H_2O$, 0.339 mmol of osmium(VIII) oxide (4% in $H_2O$) and 500 mol of 1,4-dioxane are heated to the boil with stirring and refluxed overnight. After cooling to room temperature, the solution is evaporated in a rotary evaporator, and the residue is recrystallized from acetone.

Step 3.3

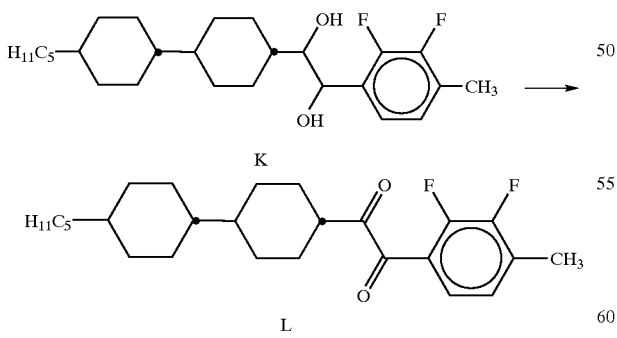

293.7 mmol of trifluoroacetic anhydride are added dropwise at −6° C. to 1.71 mol of dimethyl sulfoxide in 600 ml of dichloromethane under a nitrogen atmosphere.

The mixture is left to stir at −60° C. for 10 minutes, and a solution consisting of 97.6 mmol of K in 63 ml of dimethyl sulfoxide, 70 ml of dichloromethane and 70 ml of THF is then added dropwise. The mixture is stirred at −60° C. for 1 hour, and 91.7 ml of triethylamine are added. After the reaction is complete, the mixture is stirred at −6° C. for a further 0.5 hour. The mixture is then allowed to warm to 5° C., 1000 ml of 2N hydrochloric acid are added, and the mixture is subjected to conventional work-up.

Step 3.4

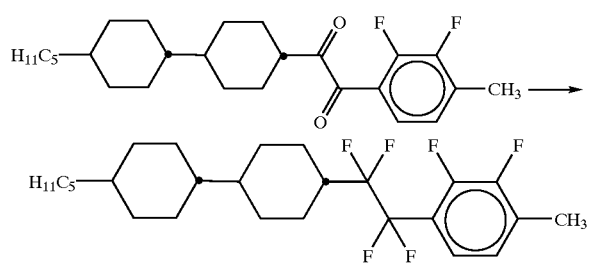

diketone L is converted into the —$C_2F_4$— compound as described in J. Am. Chem. Soc. 88, 2796–2799 (1966). In an autoclave, 0.06 mol of diketone L in 200 ml of $CH_2Cl_2$ and 0.34 mol of water are reacted with ~0.6 mol of $SF_4$. The mixture is subsequently subjected to conventional work-up.

C 39 $S_B$ 152 N 156.2 I; $\Delta\epsilon=-2.14$; $\Delta n=0.092$

The following compounds of the formula

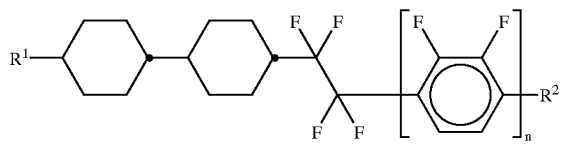

are prepared analogously:

| $R^1$ | n | $R^2$ |
|---|---|---|
| $CH_3$ | 1 | $CH_3$ |
| $C_2H_5$ | 1 | $CH_3$ |
| n-$C_3H_7$ | 1 | $CH_3$ |
| n-$C_4H_9$ | 1 | $CH_3$ |
| n-$C_6H_{13}$ | 1 | $CH_3$ |
| $CH_2$=CH | 1 | $CH_3$ |
| $CH_3$CH=CH | 1 | $CH_3$ |
| $C_3H_7$—CH=CH | 1 | $CH_3$ |
| $CH_2$=CH—$C_2H_4$ | 1 | $CH_3$ |
| $CH_3$ | 1 | $C_2H_5$ |
| $C_2H_5$ | 1 | $C_2H_5$ |
| n-$C_3H_7$ | 1 | $C_2H_5$ |
| n-$C_4H_9$ | 1 | $C_2H_5$ |
| n-$C_5H_{11}$ | 1 | $C_2H_5$ |
| n-$C_6H_{13}$ | 1 | $C_2H_5$ |
| $CH_2$=CH | 1 | $C_2H_5$ |
| $CH_3$CH=CH | 1 | $C_2H_5$ |
| $C_3H_7$—CH=CH | 1 | $C_2H_5$ |
| $CH_2$=CH—$C_2H_4$ | 1 | $C_2H_5$ |
| $CH_3$ | 1 | n-$C_3H_7$ |
| $C_2H_5$ | 1 | n-$C_3H_7$ |
| n-$C_3H_7$ | 1 | n-$C_3H_7$ |
| n-$C_4H_9$ | 1 | n-$C_3H_7$ |
| n-$C_5H_{11}$ | 1 | n-$C_3H_7$ |
| n-$C_6H_{13}$ | 1 | n-$C_3H_7$ |
| $CH_2$=CH | 1 | n-$C_3H_7$ |
| $CH_3$CH=CH | 1 | n-$C_3H_7$ |
| $C_3H_7$—CH=CH | 1 | n-$C_3H_7$ |
| $CH_2$=CH—$C_2H_4$ | 1 | n-$C_3H_7$ |
| $CH_3$ | 1 | $OCH_3$ |
| $C_2H_5$ | 1 | $OCH_3$ |

-continued

| $R^1$ | n | $R^2$ |
|---|---|---|
| n-$C_3H_7$ | 1 | $OCH_3$ |
| n-$C_4H_9$ | 1 | $OCH_3$ |
| n-$C_6H_{13}$ | 1 | $OCH_3$ |
| $CH_2$=CH | 1 | $OCH_3$ |
| $CH_3$CH=CH | 1 | $OCH_3$ |
| $C_3H_7$—CH=CH | 1 | $CCH_3$ |
| $CH_2$=CH—$C_2H_4$ | 1 | $OCH_3$ |
| $CH_3$ | 1 | $OC_2H_5$ |
| $C_2H_5$ | 1 | $OC_2H_5$ |
| n-$C_3H_7$ | 1 | $OC_2H_5$ |
| n-$C_4H_9$ | 1 | $OC_2H_5$ |
| n-$C_5H_{11}$ | 1 | $OC_2H_5$ |
| n-$C_6H_{13}$ | 1 | $OC_2H_5$ |
| $CH_2$=CH | 1 | $OC_2H_5$ |
| $CH_3$CH=CH | 1 | $OC_2H_5$ |
| $C_3H_7$—CH=CH | 1 | $OC_2H_5$ |
| $CH_2$=CH—$C_2H_4$ | 1 | $OC_2H_5$ |
| $CH_3$ | 1 | $OC_3H_7$-n |
| $C_2H_5$ | 1 | $OC_3H_7$-n |
| n-$C_3H_7$ | 1 | $OC_3H_7$-n |
| n-$C_4H_9$ | 1 | $OC_3H_7$-n |
| n-$C_5H_{11}$ | 1 | $OC_3H_7$-n |
| n-$C_6H_{13}$ | 1 | $OC_3H_7$-n |
| $CH_2$=CH | 1 | $OC_3H_7$-n |
| $CH_3$CH=CH | 1 | $OC_3H_7$-n |
| $C_3H_7$—CH=CH | 1 | $OC_3H_7$-n |
| $CH_2$=CH—$C_2H_4$ | 1 | $OC_3H_7$-n |
| $CH_3$ | 2 | $CH_3$ |
| $C_2H_5$ | 2 | $CH_3$ |
| n-$C_3H_7$ | 2 | $CH_3$ |
| n-$C_4H_9$ | 2 | $CH_3$ |
| n-$C_6H_{13}$ | 2 | $CH_3$ |
| $CH_2$=CH | 2 | $CH_3$ |
| $CH_3$CH=CH | 2 | $CH_3$ |
| $C_3H_7$—CH=CH | 2 | $CH_3$ |
| $CH_2$=CH—$C_2H_4$ | 2 | $CH_3$ |
| $CH_3$ | 2 | $C_2H_5$ |
| $C_2H_5$ | 2 | $C_2H_5$ |
| n-$C_3H_7$ | 2 | $C_2H_5$ |
| n-$C_4H_9$ | 2 | $C_2H_5$ |
| n-$C_5H_{11}$ | 2 | $C_2H_5$ |
| n-$C_6H_{13}$ | 2 | $C_2H_5$ |
| $CH_2$=CH | 2 | $C_2H_5$ |
| $CH_3$CH=CH | 2 | $C_2H_5$ |
| $C_3H_7$—CH=CH | 2 | $C_2H_5$ |
| $CH_2$=CH—$C_2H_4$ | 2 | $C_2H_5$ |
| $CH_3$ | 2 | n-$C_3H_7$ |
| $C_2H_5$ | 2 | n-$C_3H_7$ |
| n-$C_3H_7$ | 2 | n-$C_3H_7$ |
| n-$C_4H_9$ | 2 | n-$C_3H_7$ |
| n-$C_5H_{11}$ | 2 | n-$C_3H_7$ |
| n-$C_6H_{13}$ | 2 | n-$C_3H_7$ |
| $CH_2$=CH | 2 | n-$C_3H_7$ |
| $CH_3$CH=CH | 2 | n-$C_3H_7$ |
| $C_3H_7$—CH=CH | 2 | n-$C_3H_7$ |
| $CH_2$=CH—$C_2H_4$ | 2 | n-$C_3H_7$ |
| $CH_3$ | 2 | $OCH_3$ |
| $C_2H_5$ | 2 | $OCH_3$ |
| n-$C_3H_7$ | 2 | $OCH_3$ |
| n-$C_4H_9$ | 2 | $OCH_3$ |
| n-$C_6H_{13}$ | 2 | $OCH_3$ |
| $CH_2$=CH | 2 | $OCH_3$ |
| $CH_3$CH=CH | 2 | $OCH_3$ |
| $C_3H_7$—CH=CH | 2 | $OCH_3$ |
| $CH_2$=CH—$C_2H_4$ | 2 | $OCH_3$ |
| $CH_3$ | 2 | $OC_2H_5$ |
| $C_2H_5$ | 2 | $OC_2H_5$ |
| n-$C_3H_7$ | 2 | $OC_2H_5$ |
| n-$C_4H_9$ | 2 | $OC_2H_5$ |
| n-$C_5H_{11}$ | 2 | $OC_2H_5$ |
| n-$C_6H_{13}$ | 2 | $OC_2H_5$ |
| $CH_2$=CH | 2 | $OC_2H_5$ |
| $CH_3$CH=CH | 2 | $OC_2H_5$ |
| $C_3H_7$—CH=CH | 2 | $OC_2H_5$ |
| $CH_2$=CH—$C_2H_4$ | 2 | $OC_2H_5$ |
| $CH_3$ | 2 | $OC_3H_7$-n |
| $C_2H_5$ | 2 | $OC_3H_7$-n |

-continued

| $R^1$ | n | $R^2$ |
|---|---|---|
| n-$C_3H_7$ | 2 | $OC_3H_7$-n |
| n-$C_4H_9$ | 2 | $OC_3H_7$-n |
| n-$C_5H_{11}$ | 2 | $OC_3H_7$-n |
| n-$C_5H_{13}$ | 2 | $OC_3H_7$-n |
| $CH_2$=CH | 2 | $OC_3H_7$-n |
| $CH_3$CH=CH | 2 | $OC_3H_7$-n |
| $C_3H_7$—CH=CH | 2 | $OC_3H_7$-n |
| $CH_2$=CH—$C_2H_4$ | 2 | $OC_3H_7$-n |

MIXTURE EXAMPLES

Example A

An ECB-TFT mixture consisting of

| 12% | PCH-302FF |
|---|---|
| 12% | PCH-502FF |
| 14% | CCP-302FF |
| 13% | CCP-502FF |
| 8% | CCP-21FF |
| 7% | CCP-31FF |
| 6% | CCH-34 |
| 6% | CCH-35 |
| 8% | CCH-303 |
| 4% | CCH-501 |
| 10% | C—$CH_2CF_2$—CY-3-02 | has the following physical properties:

clearing point [° C.] 90.3

$\Delta n$ [589 nm, 20° C.]: +0.0798

$\Delta \epsilon$ [1 kHz, 20° C.]: −4.4

Example B

An ECB-TFT mixture consisting of

| 12% | PCH-302FF |
|---|---|
| 12% | PCH-502FF |
| 14% | CCP-302FF |
| 13% | CCP-502FF |
| 8% | CCP-21FF |
| 7% | CCP-31FF |
| 6% | CCH-34 |
| 6% | CCH-35 |
| 8% | CCH-303 |
| 4% | CCH-501 |
| 10% | C—OVF—CY-3-02 | has the following physical properties:

$\Delta \epsilon$ [1 kHz, 20° C.]: −4.4

Example C

| BCH-3F.F | 10.71% | $\Delta n$[589 nm, 20°C.]: +0.0970 |
|---|---|---|
| BCH-5F.F | 8.93% | $\Delta \epsilon$[1 kHz 20° C.]: +4.8 |
| ECCP-30$CF_3$ | 4.46% | |
| ECCP-50$CF_3$ | 4.46% | |
| CBC-333F | 1.79% | |
| CBC-53F | 1.79% | |
| CBC-55F | 1.79% | |
| PCH-6F | 7.14% | |
| PCH-7F | 5.36% | |

-continued

| | |
|---|---|
| CCP-20CF₃ | 7.14% |
| CCP30CF₃ | 10.71% |
| CCP-40CF₃ | 6.25% |
| CCP-50CF₃ | 9.82% |
| PCH-5F | 8.93% |
| CC—CHFCHF—Y-502 | 10.72% |

Example D

| | | |
|---|---|---|
| BCH-3F.F | 10.80% | Δn[589 nm, 20° C.]: +0.0966 |
| BCH-5F.F | 9.00% | Δε[1 kHz, 20° C.]: +4.7 |
| ECCP-30CF₃ | 4.50% | |
| ECCP-50CF₃ | 4.50% | |
| CBC-33F | 1.80% | |
| CBC-53F | 1.80% | |
| CBC-55F | 1.80% | |
| PCH-6F | 7.20% | |
| PCH-7F | 5.40% | |
| CCP-20CF₃ | 7.20% | |
| CCP-30CF₃ | 10.80% | |
| CCP-40CF₃ | 6.30% | |
| CCP-50CF₃ | 9.90% | |
| PCH-5F | 9.00% | |
| CC—CH₂CF₂—Y-502 | 9.96% | |

Example E

| | | |
|---|---|---|
| PCH-301 | 9.00% | Δε[1 kHz, 20° C.]: −1.6 |
| PCH-302 | 9.00% | |
| CCH-301 | 29.70% | |
| CCN-47 | 9.90% | |
| CCN-55 | 9.00% | |
| CBC-33F | 4.50% | |
| CBC-53F | 4.50% | |
| CBC-55F | 4.50% | |
| CBC-33 | 4.50% | |
| CBC-53 | 5.40% | |
| CC—CH₂CF₂—Y-502 | 9.99% | |

Example F

| | | |
|---|---|---|
| PCH-301 | 9.00% | clearing point [° C.]: +88.1 |
| PCH-302 | 9.00% | Δε[1 kHz, 20° C.]: −1.5 |
| CCH-301 | 29.69% | |
| CCN-47 | 9.90% | |
| CCN-55 | 9.00% | |
| CBC-33F | 4.50% | |
| CBC-53F | 4.50% | |
| CBC-55F | 4.50% | |
| CBC-33 | 4.50% | |
| CBC-53 | 5.40% | |
| CC—CF₂CF₂—Y-502 | 10.02% | |

Example G

| | | |
|---|---|---|
| PCH-6F | 7.20% | clearing point [° C.]: +98.4 |
| PCH-7F | 5.40% | Δn[589 nm, 20° C.]: +0.0960 |
| CCP-20CF₃ | 7.20% | Δε[1 kHz, 20° C.]: +4.7 |
| CCP-30CF₃ | 10.80% | |
| CCP-40CF₃ | 6.30% | |

-continued

| | |
|---|---|
| PCH-5F | 9.00% |
| CCP-50CF₃ | 9.90% |
| BCH-3F.F | 10.80% |
| BCH-5F.F | 9.00% |
| ECCP-30CF₃ | 4.50% |
| ECCP-50CF₃ | 4.50% |
| CBC-33F | 1.80% |
| CBC-53F | 1.80% |
| CBC-55F | 1.80% |
| CC—CF₂CF₂—Y-51 | 10.00% |

Example H

| | | |
|---|---|---|
| PCH-301 | 8.97% | Δε[1 kHz, 20° C.]: −1.4 |
| PCH-302 | 8.97% | |
| CCH-301 | 29.58% | |
| CCN-47 | 9.86% | |
| CCN-55 | 8.97% | |
| CBC-33F | 4.48% | |
| CBC-53F | 4.48% | |
| CBC-55F | 4.48% | |
| CBC-33 | 4.48% | |
| CBC-53 | 5.38% | |
| CC—CHFCHF-502 | 10.35% | |

What is claimed is:
1. A liquid-crystalline compound of the formula I

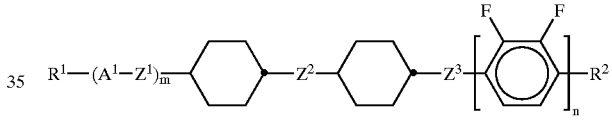

in which
R¹ and R² are each, independently of one another, an alkyl or alkenyl radical having 1 to 15 carbon atoms which is unsubstituted, monosubstituted by CN or CF₃ or at least monosubstituted by halogen, where one or more CH₂ groups in these radicals may also, in each case independently of one another, be replaced by —O—, —S—, —◊—, —CO—, —CO—O—, —O—CO— or —O—CO—O— in such a way that O atoms are not linked directly to one another, A¹ (a) is a trans-1,4-cyclohexylene radical, in which, in addition, one or more non-adjacent CH₂ groups may, in each case, be replaced by —O— or —S—,
  (b) a 1,4-phenylene radical, in which, in addition, one or two CH groups may, in each case, be replaced by N,
  (c) a 1,4-cyclohexenylene radical,
  (d) a radical from the group consisting of 1,4-bicyclo[2.2.2]octylene, piperidine-1,4-diyl, naphthalene-2,6-diyl, decahydronaphthalene-2,6-diyl and 1,2,3,4-tetrahydronaphthalene-2,6-diyl,
  where the radicals (a), (b) and (c) are each, optionally, monosubstituted or polysubstituted by CN or fluorine, Z¹, Z²
and Z³ are each, independently of one another, —CO—O—, —O—CO—, —CH₂O—, —OCH₂—, —CH₂CH₂—, —CH=CH—, —C≡C—, —CF₂O—, —OCF₂—, —(CH₂)₄—, a single bond,

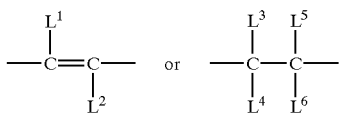

$L^1$ to $L^6$ are each, independently of one another, H or F, wherein at least one of the radicals $L^1$ and $L^2$ is F or at least one of $L^3$ to $L^6$ is F, m is 0 or 1, and n is 1 or 2, with the proviso that at least one bridge $Z^1$, $Z^2$ or $Z^3$ is

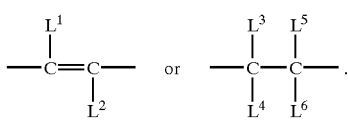

2. A liquid-crystalline compound according to claim 1, wherein $R^1$ is alkyl or alkenyl.

3. A liquid-crystalline compound according to claim 1, wherein $R^2$ is alkyl or alkoxy.

4. A liquid-crystalline compound according to claim 1, wherein m=0.

5. A liquid-crystalline compound according to claim 1, wherein $Z^2$ is —$CF_2CF_2$—.

6. A liquid-crystalline compound according to claim 1, wherein $Z^3$ is —$CF_2CF_2$—.

7. A liquid-crystalline compound according to claim 1, wherein $Z^2$ and $L^3$ are —$CH_2CF_2$—.

8. A liquid-crystalline compound according to claim 1, wherein $Z^2$ is —$CH_2CH_2$—.

9. A liquid-crystalline compound according to claim 1, wherein said compound is of formulae I1 to I5

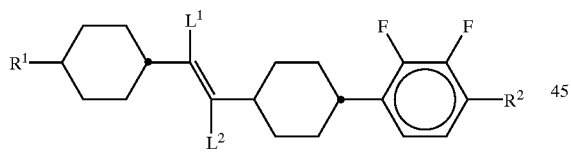

I1

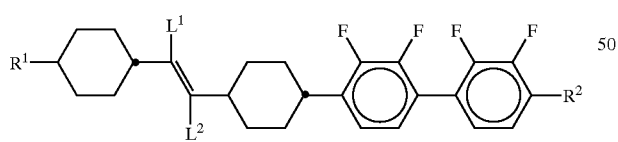

I2

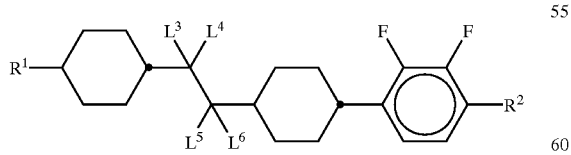

I3

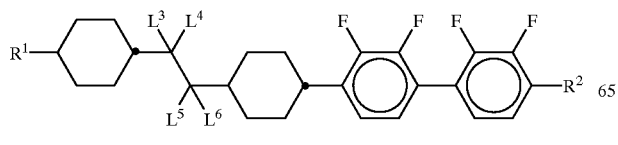

I4

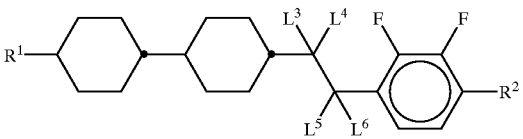

I5

10. A compound according to claim 9, wherein said compound is of formula I3 and $L^3$ and $L^4$ are each H and $L^5$ and $L^6$ are each F or $L^3$–$L^6$ are all each F.

11. A liquid-crystalline medium comprising at least two liquid-crystalline components, wherein said composition comprises at least one compound of the formula I.

12. In a liquid-crystal display element containing a liquid-crystalline medium, the improvement wherein said medium is in accordance with claim 11.

13. In an electro-optical display element containing a liquid-crystalline medium, the improvement wherein said medium is in accordance with claim 11.

14. A process for the preparation of —$C_2F_4$-bridged alkyl compounds starting from compounds which contain a

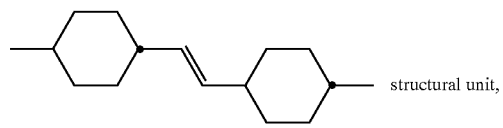 structural unit, said process comprising:

converting the double bond into a dihydroxyl compound which contains a

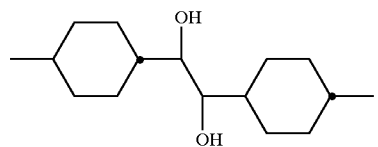

structural unit using N-methylmorpholine N-oxide and a catalytic amount of $OsO_4$; oxidizing the dihydroxyl compound to give a diketone compound having the following structural unit

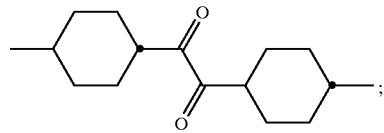

and reacting the diketone compound with $SF_4$ under reduced pressure to give a compound having a —$C_2F_4$— structural unit.

15. A compound accordint to claim 1, wherein $R^1$ is a straight-chain alkyl, 1E-alkenyl or 3E-alkenyl.

16. A compound accordning to claim 1, wherein $R^2$ is a straight-chain alkoxy having 1–5 carbon atoms or alkyl having 1–5 carbon atoms.

17. A compound according to claim 1, wherein $R^1$ is alkoxy or oxaalkyl.

18. A compound according to claim 1, wherein $Z^1$'$Z^2$, and $Z^3$ are each a single bond or —$C_2H_4$— with the proviso that at least one of $Z^1$'$Z^2$, or $Z^3$ is

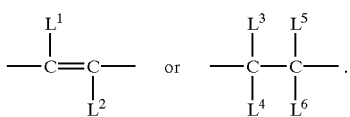

19. A compound according to claim 1, wherein $R^1$ and $R^2$ each have 2–12 carbon atoms.

20. A compound according to claim 1, wherein $R^1$ and $R^2$ are each, independently of one another, an alkyl or alkenyl radical having 1–15 carbon atoms which is unsubstituted, monosubstituted by CN or $CF_3$ or at least monosubstituted by halogen, wherein one $CH_2$ group is optionally replaced by —O— or —CH=CH—.

21. A compound according to claim 9, wherein said compound is of formula I1 or I3.

22. A compound according to claim 9, wherein said compound is of formula I1 or I2 and $R^2$ is methoxy, ethoxy, propoxy, butoxy, pentoxy, hexoxy, methyl, ethyl, n-propyl, n-butyl, n-pentyl, or n-hexyl.

23. A compound according to claim 1, wherein $R^1$ is preferably ethyl, propyl, n-butyl, n-pentyl, n-hexyl, vinyl, 1E-propenyl, 1E-butenyl, 1E-pentenyl, 1E-hexenyl, 1E-heptenyl, 1E-octenyl, 1E-nonenyl, 1E-decenyl, allyl, 2Z-butenyl, 2Z-pentenyl, 2Z-hexenyl, 2Z-heptenyl, 2Z-octenyl, 2Z-nonenyl, 2Z-decenyl, 3E-butenyl, 3E-pentenyl, 3E-hexenyl, 3E-heptenyl, 3E-octenyl, 3E-nonenyl or 4E-pentenyl.

24. A compound according to claim 1, wherein $L^1$ and $L^2$ are each F.

25. A compound according to claim 1, wherein $L^1$ is F and $L^2$ is H or F.

26. A compound according to claim 1, wherein $L^1$ is H or F and $L^2$ is F.

27. A liquid crystalline medium according to claim 11, wherein said medium contains 0.1–99 wt % of compounds according to formula I.

28. A liquid crystalline medium according to claim 11, wherein said medium contains 10–95 wt % of one or more compounds of formula I.

29. A liquid crystalline medium according to claim 11, wherein said medium contain 0.1–50 wt % of one or more compounds of formula I.

30. A liquid crystalline medium according to claim 11, wherein said medium contain 0.5–30 wt % of one or more compounds of formula I.

* * * * *